(12) United States Patent
Bedard et al.

(10) Patent No.: US 8,986,397 B2
(45) Date of Patent: Mar. 24, 2015

(54) INSTRUMENTED PROSTHETIC FOOT

(75) Inventors: Stephane Bedard, Quebec (CA);
Pierre-Olivier Roy, Quebec (CA)

(73) Assignee: Victhom Human Bionics, Inc., Quebec (CA)

( * ) Notice: Subject to any disclaimer, the term of this patent is extended or adjusted under 35 U.S.C. 154(b) by 322 days.

(21) Appl. No.: 13/354,188

(22) Filed: Jan. 19, 2012

(65) Prior Publication Data

US 2012/0191221 A1    Jul. 26, 2012

Related U.S. Application Data

(60) Continuation of application No. 11/881,964, filed on Jul. 31, 2007, now abandoned, which is a division of application No. 10/715,989, filed on Nov. 18, 2003, now abandoned.

(51) Int. Cl.
| | | |
|---|---|---|
| *A61F 2/64* | (2006.01) | |
| *A61F 2/68* | (2006.01) | |
| *A61F 2/66* | (2006.01) | |
| A61F 2/72 | (2006.01) | |
| A61F 2/50 | (2006.01) | |

(Continued)

(52) U.S. Cl.
CPC ... *A61F 2/68* (2013.01); *A61F 2/66* (2013.01); *A61F 2/72* (2013.01); *A61F 2002/5001* (2013.01); *A61F 2002/5003* (2013.01); *A61F 2002/5007* (2013.01); *A61F 2002/6621* (2013.01); *A61F 2002/6642* (2013.01); *A61F 2002/665* (2013.01); *A61F 2002/6685* (2013.01); *A61F 2002/705* (2013.01); *A61F 2002/7635* (2013.01); *A61F 2002/764* (2013.01); *A61F 2002/7685* (2013.01)

USPC .................................. 623/47; 623/40; 623/53

(58) Field of Classification Search
USPC ............................. 623/27–29, 32, 40, 47, 53
See application file for complete search history.

(56) References Cited

U.S. PATENT DOCUMENTS

| | | |
|---|---|---|
| 2,568,051 A | 9/1951 | Catranis |
| 2,619,652 A | 12/1952 | Vesper |
| 2,843,853 A | 7/1958 | Mauch |

(Continued)

FOREIGN PATENT DOCUMENTS

| | | |
|---|---|---|
| CH | 543277 | 12/1973 |
| CN | 2043873 | 9/1989 |

(Continued)

OTHER PUBLICATIONS

Abbas, et al., Neural Network Control of Functional Neuromuscular Stimulation Systems: Computer Stimulation Studies, 1995.

(Continued)

*Primary Examiner* — Howie Matthews
(74) *Attorney, Agent, or Firm* — Knobbe, Martens, Olson & Bear, LLP

(57) ABSTRACT

The present invention discloses an instrumented prosthetic foot for use with an actuated leg prosthesis controlled by a controller, the instrumented prosthetic foot comprising a connector to connect the instrumented prosthetic foot to the leg prosthesis, an ankle structure connected to the connector, a ground engaging member connected to the ankle, at least one sensor for detecting changes in weight distribution along the foot, and an interface for transmitting signals from the sensor to the controller.

17 Claims, 15 Drawing Sheets

(51) Int. Cl.
*A61F 2/70* (2006.01)
*A61F 2/76* (2006.01)

(56) References Cited

U.S. PATENT DOCUMENTS

| | | |
|---|---|---|
| 2,859,451 A | 11/1958 | Mauch |
| 3,316,558 A | 5/1967 | Mortensen |
| 3,417,409 A | 12/1968 | Prahl |
| 3,501,776 A | 3/1970 | Beeker et al. |
| 3,659,294 A | 5/1972 | Glabiszewski |
| 3,701,368 A | 10/1972 | Stern |
| 3,791,375 A | 2/1974 | Pfeiffer |
| 3,820,168 A | 6/1974 | Horvath |
| 3,866,246 A | 2/1975 | Seamone et al. |
| 3,871,032 A | 3/1975 | Karas |
| 3,995,324 A | 12/1976 | Burch |
| 4,005,496 A | 2/1977 | Wilkes |
| 4,023,215 A | 5/1977 | Moore |
| 4,030,141 A | 6/1977 | Graupe |
| 4,064,569 A | 12/1977 | Campbell |
| 4,065,815 A | 1/1978 | Sen-Jung |
| 4,100,918 A | 7/1978 | Glancy |
| 4,179,759 A | 12/1979 | Smith |
| 4,209,860 A | 7/1980 | Graupe |
| 4,212,087 A | 7/1980 | Mortensen |
| 4,310,932 A | 1/1982 | Nader et al. |
| 4,314,379 A | 2/1982 | Tanie et al. |
| 4,354,676 A | 10/1982 | Ariel |
| 4,386,891 A | 6/1983 | Riefel et al. |
| 4,387,472 A | 6/1983 | Wilson |
| 4,433,679 A | 2/1984 | Mauldin et al. |
| 4,458,367 A | 7/1984 | May |
| 4,518,307 A | 5/1985 | Bloch |
| 4,521,924 A | 6/1985 | Jacobsen et al. |
| 4,556,956 A | 12/1985 | Dickenson et al. |
| 4,558,704 A | 12/1985 | Petrofsky |
| 4,569,352 A | 2/1986 | Petrofsky et al. |
| 4,578,083 A | 3/1986 | Williams |
| 4,600,357 A | 7/1986 | Coules |
| 4,602,619 A | 7/1986 | Wolf et al. |
| 4,617,920 A | 10/1986 | Carsalade |
| 4,649,934 A | 3/1987 | Fraser et al. |
| 4,657,000 A | 4/1987 | Hepburn |
| 4,657,470 A | 4/1987 | Clarke et al. |
| 4,685,926 A | 8/1987 | Haupt |
| 4,685,927 A | 8/1987 | Haupt |
| 4,711,242 A | 12/1987 | Petrofsky |
| 4,726,404 A | 2/1988 | Haber et al. |
| 4,730,625 A | 3/1988 | Fraser et al. |
| 4,760,850 A | 8/1988 | Phillips et al. |
| 4,770,662 A | 9/1988 | Giampapa |
| 4,776,326 A | 10/1988 | Roung et al. |
| 4,776,852 A | 10/1988 | Rubic |
| 4,790,522 A | 12/1988 | Drutchas |
| 4,795,474 A | 1/1989 | Horvath |
| 4,805,455 A | 2/1989 | DelGiorno et al. |
| 4,808,187 A | 2/1989 | Patterson et al. |
| 4,814,661 A | 3/1989 | Ratzlaff et al. |
| 4,838,251 A | 6/1989 | Chignon et al. |
| 4,843,921 A | 7/1989 | Kremer |
| 4,854,428 A | 8/1989 | Horvath |
| 4,865,024 A | 9/1989 | Hensley et al. |
| 4,872,803 A | 10/1989 | Asakawa |
| 4,876,944 A | 10/1989 | Wilson et al. |
| 4,878,913 A | 11/1989 | Aebischer et al. |
| 4,892,554 A | 1/1990 | Robinson |
| 4,893,648 A | 1/1990 | Horvath |
| 4,919,418 A | 4/1990 | Miller |
| 4,928,676 A | 5/1990 | Pansiera |
| 4,944,755 A | 7/1990 | Hennequin et al. |
| 4,958,705 A | 9/1990 | Horvath |
| 4,989,161 A | 1/1991 | Oaki |
| 4,994,086 A | 2/1991 | Edwards |
| 5,020,790 A | 6/1991 | Beard et al. |
| 5,033,291 A | 7/1991 | Podoloff et al. |
| 5,044,360 A | 9/1991 | Janke |
| 5,062,673 A | 11/1991 | Mimura |
| 5,062,856 A | 11/1991 | Sawamura et al. |
| 5,062,857 A | 11/1991 | Berringer |
| 5,086,785 A | 2/1992 | Gentile et al. |
| 5,092,902 A | 3/1992 | Adams et al. |
| 5,112,296 A | 5/1992 | Beard et al. |
| 5,112,356 A | 5/1992 | Harris et al. |
| 5,139,525 A | 8/1992 | Kristinsson |
| 5,153,496 A | 10/1992 | LaForge |
| 5,174,168 A | 12/1992 | Takagi et al. |
| 5,181,931 A | 1/1993 | Van de Veen |
| 5,197,488 A | 3/1993 | Kovacevic |
| 5,201,772 A | 4/1993 | Maxwell |
| 5,217,500 A | 6/1993 | Phillips |
| 5,219,365 A | 6/1993 | Sabolich |
| 5,230,672 A | 7/1993 | Brown et al. |
| 5,246,465 A | 9/1993 | Rincoe et al. |
| 5,252,102 A | 10/1993 | Singer et al. |
| 5,252,901 A | 10/1993 | Ozawa et al. |
| 5,253,656 A | 10/1993 | Rincoe |
| 5,265,890 A | 11/1993 | Balsells |
| 5,277,281 A | 1/1994 | Carlson et al. |
| 5,282,460 A | 2/1994 | Boldt |
| 5,284,330 A | 2/1994 | Carlson et al. |
| 5,314,498 A | 5/1994 | Gramnas |
| 5,323,650 A | 6/1994 | Fullen et al. |
| 5,327,790 A | 7/1994 | Levin et al. |
| 5,336,269 A | 8/1994 | Smits |
| 5,357,696 A | 10/1994 | Gray et al. |
| 5,376,128 A | 12/1994 | Bozeman, Jr. |
| 5,376,133 A | 12/1994 | Gramnas |
| 5,376,137 A | 12/1994 | Shorter et al. |
| 5,382,373 A | 1/1995 | Carlson et al. |
| 5,383,939 A | 1/1995 | James |
| 5,394,132 A | 2/1995 | Poil |
| 5,397,287 A | 3/1995 | Lindfors |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,437,611 A | 8/1995 | Stern |
| 5,443,521 A | 8/1995 | Knoth et al. |
| 5,443,524 A | 8/1995 | Sawamura et al. |
| 5,472,412 A | 12/1995 | Knoth |
| 5,476,441 A | 12/1995 | Durfee et al. |
| 5,504,415 A | 4/1996 | Podrazhansky et al. |
| D372,536 S | 8/1996 | Grifka |
| 5,545,232 A | 8/1996 | Van de Veen |
| 5,545,233 A | 8/1996 | Fitzlaff |
| 5,551,525 A | 9/1996 | Pack et al. |
| 5,563,458 A | 10/1996 | Ericson |
| 5,566,479 A | 10/1996 | Gray et al. |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,583,476 A | 12/1996 | Langford |
| 5,586,557 A | 12/1996 | Nelson et al. |
| 5,624,389 A | 4/1997 | Zepf |
| 5,642,096 A | 6/1997 | Leyerer et al. |
| 5,645,590 A | 7/1997 | Van de Veen |
| 5,645,752 A | 7/1997 | Weiss et al. |
| 5,650,704 A | 7/1997 | Pratt et al. |
| 5,656,915 A | 8/1997 | Eaves |
| D383,542 S | 9/1997 | Wellershaus et al. |
| 5,662,693 A | 9/1997 | Johnson et al. |
| 5,670,077 A | 9/1997 | Carlson et al. |
| 5,678,448 A | 10/1997 | Fullen et al. |
| 5,683,615 A | 11/1997 | Munoz |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,728,174 A | 3/1998 | Fitzlaff |

(56) References Cited

U.S. PATENT DOCUMENTS

| | | | |
|---|---|---|---|
| 5,746,774 | A | 5/1998 | Kramer |
| 5,749,533 | A | 5/1998 | Daniels |
| 5,755,812 | A | 5/1998 | Becker et al. |
| 5,755,813 | A | 5/1998 | Krukenberg |
| 5,779,735 | A | 7/1998 | Molino |
| 5,800,561 | A | 9/1998 | Rodriguez |
| 5,800,568 | A | 9/1998 | Atkinson et al. |
| 5,810,752 | A | 9/1998 | Grifka |
| 5,823,309 | A | 10/1998 | Gopalswamy et al. |
| D402,368 | S | 12/1998 | Holzapfel |
| 5,842,547 | A | 12/1998 | Carlson et al. |
| D407,490 | S | 3/1999 | Zepf et al. |
| 5,878,851 | A | 3/1999 | Carlson et al. |
| 5,888,212 | A | 3/1999 | Petrofsky et al. |
| 5,888,213 | A | 3/1999 | Sears et al. |
| 5,888,236 | A | 3/1999 | Van de Veen |
| 5,888,239 | A | 3/1999 | Wellershaus et al. |
| 5,888,246 | A | 3/1999 | Gow |
| 5,893,891 | A | 4/1999 | Zahedi |
| 5,895,430 | A | 4/1999 | O'Connor |
| 5,899,869 | A | 5/1999 | Barrack, Jr. et al. |
| 5,900,184 | A | 5/1999 | Weiss et al. |
| 5,906,767 | A | 5/1999 | Karol et al. |
| 5,919,149 | A | 7/1999 | Allum |
| 5,929,332 | A | 7/1999 | Brown |
| 5,941,913 | A | 8/1999 | Woolnough et al. |
| 5,947,238 | A | 9/1999 | Jolly et al. |
| 5,948,021 | A | 9/1999 | Radcliffe |
| 5,955,667 | A | 9/1999 | Fyfe |
| 5,957,981 | A | 9/1999 | Grammas |
| 5,960,918 | A | 10/1999 | Moser et al. |
| 5,967,273 | A | 10/1999 | Hampton |
| 5,972,035 | A | 10/1999 | Blatchford |
| 5,982,156 | A | 11/1999 | Weimer et al. |
| 5,998,930 | A | 12/1999 | Upadhyay et al. |
| 6,006,412 | A | 12/1999 | Bergmann et al. |
| 6,007,582 | A | 12/1999 | May |
| RE36,521 | E | 1/2000 | Hiemisch |
| 6,039,091 | A | 3/2000 | Rodgers et al. |
| 6,061,577 | A | 5/2000 | Andrieu et al. |
| 6,080,123 | A | 6/2000 | Pansiera |
| 6,086,616 | A | 7/2000 | Okuda et al. |
| 6,091,977 | A | 7/2000 | Tarjan et al. |
| 6,093,162 | A | 7/2000 | Fairleigh et al. |
| 6,095,486 | A | 8/2000 | Ivers et al. |
| 6,113,642 | A | 9/2000 | Petrofsky et al. |
| 6,117,177 | A | 9/2000 | Chen et al. |
| 6,129,690 | A | 10/2000 | Hamlin et al. |
| 6,139,586 | A | 10/2000 | Wagner et al. |
| 6,151,624 | A | 11/2000 | Teare et al. |
| 6,164,967 | A | 12/2000 | Sale et al. |
| 6,165,226 | A | 12/2000 | Wagner |
| 6,168,634 | B1 | 1/2001 | Schmitz |
| 6,183,425 | B1 | 2/2001 | Whalen et al. |
| 6,185,614 | B1 | 2/2001 | Cuomo et al. |
| 6,187,051 | B1 | 2/2001 | van de Veen |
| D439,339 | S | 3/2001 | Sawatzki |
| 6,195,921 | B1 | 3/2001 | Truong |
| 6,206,932 | B1 | 3/2001 | Johnson |
| 6,206,933 | B1 | 3/2001 | Shorter et al. |
| 6,206,934 | B1 | 3/2001 | Phillips |
| 6,241,775 | B1 | 6/2001 | Blatchford |
| D446,304 | S | 8/2001 | Sawatzki |
| 6,301,964 | B1 | 10/2001 | Fyfe et al. |
| 6,342,076 | B1 | 1/2002 | Lundborg |
| 6,350,286 | B1 | 2/2002 | Atkinson et al. |
| 6,352,144 | B1 | 3/2002 | Brooks |
| 6,361,570 | B1 | 3/2002 | Gow |
| 6,373,152 | B1 | 4/2002 | Wang et al. |
| 6,395,193 | B1 | 5/2002 | Kintz et al. |
| 6,409,695 | B1 | 6/2002 | Connelly |
| 6,423,098 | B1 | 7/2002 | Biedermann |
| 6,425,925 | B1 | 7/2002 | Grundei |
| 6,430,843 | B1 | 8/2002 | Potter et al. |
| 6,436,149 | B1 | 8/2002 | Rincoe |
| 6,443,993 | B1 | 9/2002 | Koniuk |
| 6,443,995 | B1 | 9/2002 | Townsend et al. |
| 6,451,481 | B1 | 9/2002 | Lee et al. |
| 6,485,519 | B2 | 11/2002 | Meyers et al. |
| 6,494,039 | B2 | 12/2002 | Pratt et al. |
| 6,500,210 | B1 | 12/2002 | Sabolich et al. |
| 6,513,381 | B2 | 2/2003 | Fyfe et al. |
| 6,517,585 | B1 | 2/2003 | Zahedi et al. |
| 6,522,266 | B1 | 2/2003 | Soehren et al. |
| 6,537,322 | B1 | 3/2003 | Johnson et al. |
| 6,574,655 | B1 | 6/2003 | Libert et al. |
| 6,587,728 | B2 | 7/2003 | Fang et al. |
| 6,589,287 | B2 | 7/2003 | Lundborg |
| 6,599,439 | B2 | 7/2003 | Iyengar et al. |
| 6,602,295 | B1 | 8/2003 | Doddroe et al. |
| 6,610,101 | B2 | 8/2003 | Herr et al. |
| 6,613,097 | B1 | 9/2003 | Cooper |
| 6,645,252 | B2 | 11/2003 | Asai et al. |
| 6,663,673 | B2 | 12/2003 | Christensen |
| 6,671,531 | B2 | 12/2003 | Al-Ali et al. |
| 6,679,920 | B2 | 1/2004 | Biedermann et al. |
| 6,695,885 | B2 | 2/2004 | Schulman et al. |
| 6,719,806 | B1 | 4/2004 | Zahedi et al. |
| 6,733,180 | B2 | 5/2004 | Nakamura |
| 6,740,123 | B2 | 5/2004 | Davalli et al. |
| 6,740,125 | B2 | 5/2004 | Mosler |
| 6,743,260 | B2 | 6/2004 | Townsend et al. |
| 6,755,870 | B1 | 6/2004 | Biedermann et al. |
| 6,761,743 | B1 | 7/2004 | Johnson |
| 6,764,520 | B2 | 7/2004 | Deffenbaugh et al. |
| 6,770,045 | B2 | 8/2004 | Naft et al. |
| 6,780,343 | B2 | 8/2004 | Hata et al. |
| 6,805,677 | B2 | 10/2004 | Simmons |
| 6,811,571 | B1 | 11/2004 | Phillips |
| 6,813,582 | B2 | 11/2004 | Levi et al. |
| D499,487 | S | 12/2004 | Bedard et al. |
| D501,925 | S | 2/2005 | Bedard et al. |
| 6,855,170 | B2 | 2/2005 | Gramnas |
| 6,875,241 | B2 | 4/2005 | Christensen |
| 6,876,135 | B2 | 4/2005 | Pelrine |
| 6,908,488 | B2 | 6/2005 | Passivaara |
| 6,910,331 | B2 | 6/2005 | Asai et al. |
| 6,918,308 | B2 | 7/2005 | Biedermann |
| 6,966,882 | B2 | 11/2005 | Horst |
| 6,966,933 | B2 | 11/2005 | Christensen |
| 7,025,792 | B2 | 4/2006 | Collier |
| 7,029,500 | B2 | 4/2006 | Martin |
| 7,042,197 | B2 | 5/2006 | Turner et al. |
| 7,063,727 | B2 | 6/2006 | Phillips et al. |
| 7,066,896 | B1 | 6/2006 | Kiselik |
| 7,101,487 | B2 | 9/2006 | Hsu et al. |
| 7,118,601 | B2 | 10/2006 | Yasui |
| 7,137,998 | B2 | 11/2006 | Bedard |
| 7,147,667 | B2 | 12/2006 | Bedard |
| 7,150,762 | B2 | 12/2006 | Caspers |
| 7,164,967 | B2 | 1/2007 | Etienne-Cummings et al. |
| 7,182,738 | B2 | 2/2007 | Bonutti et al. |
| 7,198,071 | B2 | 4/2007 | Bisbee, III et al. |
| 7,209,788 | B2 * | 4/2007 | Nicolelis et al. ............... 607/48 |
| 7,295,892 | B2 | 11/2007 | Herr et al. |
| 7,314,490 | B2 | 1/2008 | Bedard et al. |
| 7,381,192 | B2 | 6/2008 | Brodard |
| 7,396,337 | B2 | 7/2008 | McBean et al. |
| 7,410,338 | B2 | 8/2008 | Schiele et al. |
| 7,410,471 | B1 | 8/2008 | Campbell et al. |
| 7,462,201 | B2 | 12/2008 | Christensen |
| 7,503,900 | B2 | 3/2009 | Goswami |
| 7,520,904 | B2 | 4/2009 | Christensen |
| 7,575,602 | B2 | 8/2009 | Amirouche et al. |
| 7,641,700 | B2 | 1/2010 | Yasui |
| 7,736,394 | B2 | 6/2010 | Bedard et al. |
| 7,815,689 | B2 | 10/2010 | Bedard et al. |
| 7,867,284 | B2 | 1/2011 | Bedard |
| 7,918,808 | B2 | 4/2011 | Simmons |
| 7,955,398 | B2 | 6/2011 | Bedard et al. |
| 8,007,544 | B2 | 8/2011 | Jonsson et al. |
| 8,075,633 | B2 | 12/2011 | Herr et al. |
| 8,109,890 | B2 | 2/2012 | Kamiar et al. |
| 8,231,687 | B2 | 7/2012 | Bedard et al. |

(56) References Cited

U.S. PATENT DOCUMENTS

| | | | |
|---|---|---|---|
| 8,287,477 | B1 | 10/2012 | Herr et al. |
| 8,323,354 | B2 | 12/2012 | Bedard et al. |
| 2002/0087216 | A1 | 7/2002 | Atkinson et al. |
| 2003/0019700 | A1 | 1/2003 | Wittig |
| 2003/0120353 | A1 | 6/2003 | Christensen |
| 2003/0149600 | A1 | 8/2003 | Williams |
| 2004/0064195 | A1 | 4/2004 | Herr |
| 2004/0083007 | A1 | 4/2004 | Molino et al. |
| 2005/0107889 | A1 | 5/2005 | Bedard et al. |
| 2007/0027557 | A1 | 2/2007 | Jonsson et al. |
| 2008/0046096 | A1 | 2/2008 | Bedard et al. |
| 2010/0262260 | A1 | 10/2010 | Bedard et al. |
| 2011/0130847 | A1 | 6/2011 | Bedard et al. |
| 2011/0137429 | A1 | 6/2011 | Bedard |
| 2013/0035769 | A1 | 2/2013 | Bedard et al. |
| 2013/0297041 | A1 | 11/2013 | Bedard et al. |

FOREIGN PATENT DOCUMENTS

| | | |
|---|---|---|
| CN | 1215614 | 5/1999 |
| CN | 2400072 Y | 10/2000 |
| DE | 3543291 | 6/1987 |
| DE | 3923056 | 1/1991 |
| DE | 3923057 | 1/1991 |
| DE | 4229330 | 3/1994 |
| DE | 195 21 464 A | 3/1997 |
| EP | 0358056 | 3/1990 |
| EP | 0380060 | 8/1990 |
| EP | 0654254 | 5/1995 |
| EP | 0902547 | 3/1999 |
| EP | 1125825 | 1/2001 |
| EP | 1107420 | 6/2001 |
| EP | 1166726 | 1/2002 |
| EP | 1169982 | 1/2002 |
| FR | 2293185 | 7/1976 |
| FR | 2623086 A1 | 5/1989 |
| FR | 2816463 | 5/2002 |
| GB | 2201260 | 8/1988 |
| GB | 2244006 | 11/1991 |
| GB | 2260495 | 4/1993 |
| GB | 2301776 | 12/1996 |
| GB | 2302949 | 2/1997 |
| GB | 2367753 | 8/1998 |
| GB | 2338653 | 12/1999 |
| GB | 2343848 | 5/2000 |
| JP | 59-32453 | 2/1984 |
| JP | 59-71747 | 4/1984 |
| JP | 60-081530 | 5/1985 |
| JP | 59-189843 | 10/1985 |
| JP | 01-244748 | 9/1989 |
| JP | 03-181633 | 8/1991 |
| JP | 04-78337 | 3/1992 |
| JP | 05-123348 | 5/1993 |
| JP | 5-161668 | 6/1993 |
| JP | 7-24766 | 1/1995 |
| JP | 11-000345 | 1/1999 |
| JP | 11-056885 | 3/1999 |
| JP | 11-215793 | 8/1999 |
| JP | 2001-277175 | 10/2001 |
| JP | 2002-191654 | 7/2002 |
| JP | 2005-500 | 1/2005 |
| KR | 2002/0041137 | 6/2002 |
| SU | 1447366 | 12/1988 |
| SU | 1731210 | 5/1992 |
| WO | WO 94/06374 | 3/1994 |
| WO | WO 94/09727 | 5/1994 |
| WO | WO 95/26171 | 10/1995 |
| WO | WO 96/39110 | 12/1996 |
| WO | WO 96/41599 | 12/1996 |
| WO | WO 97/00661 | 1/1997 |
| WO | WO 97/27822 | 8/1997 |
| WO | WO 98/2552 A | 6/1998 |
| WO | WO 98/25552 A | 6/1998 |
| WO | WO 98/38951 | 9/1998 |
| WO | WO 99/00075 | 1/1999 |
| WO | WO 99/05991 | 2/1999 |
| WO | WO 99/29272 A | 6/1999 |
| WO | WO 99/55261 | 11/1999 |
| WO | WO 00/27318 | 5/2000 |
| WO | WO 01/17466 | 3/2001 |
| WO | WO 02/80825 | 10/2002 |
| WO | WO 03/003953 | 1/2003 |
| WO | WO 03/088373 | 10/2003 |
| WO | WO 2004/017871 A | 3/2004 |

OTHER PUBLICATIONS

Advanced Materials & Processes, Sep. 2003, vol. 9, Issue 161, pp. 29-30, 3 pages.

Kamiar Aminian et al., *Estimation of Speed and Incline of Walking Using Neural Network*, IEEE Transactions on Instrumentation and Measurement, vol. 44, No. 3, Jun. 1995, at 743.

Andrews, Bij., et al., Hybrid FES Orthosis Incorporating Closed Loop Control and Sensory Feedback, *J. Biomed. Eng.* 1988, vol. 10, April, 189-195.

Bachmann, et al., Inertial and Magnetic Tracking of Limb Segment Orientation for Inserting Humans into Synthetic Environments, 2000.

Bar, A., et al., "Adaptive Microcomputer Control of an Artificial Knee in Level Walking," J. Biomechanical Eng., vol. 5, pp. 145-150, 1983.

Baten, Inertial Sensing in Ambulatory Back Load Estimation, 1996.

Benedetti, Gait Analysis of Patients Affected by Post-Traumatic Ankle Arthrosis Treated with Osteochondral Allograft Transplantation, SIAMOC 2006 Congress Abstracts/Gait & Posture.

Blaya, Force-Controllable Ankle Foot Orthosis (AFO) to Assist Drop Foot Gait, Feb. 2003 (believed to be catalogued on or after Jul. 8, 2003.

Blumentritt, Siegmar, Ph.D., et al.; "Design Principles, Biomedical Data and Clinical Experience with a Polycentric Knee Offering Controlled Stance Phase Knee Flexion: A Preliminary Report", 1997, Journal of Prothetics and Orthotics, vol. 9, No. 1, 18-24.

Bogert, et al., A Method for Inverse Dynamic Analysis Using Accelerometry, 1995.

Bortz, A New Mathematical Formulation for Strapdown Inertial Navigation, 1971.

Bouten, A Triaxial Accelerometer and Portable Data Processing Unit for the Assessment of Daily Physical Activity, 1997.

Bouten, Carlifin V., et al., Assessment of Energy Expenditure for Physical Activity Using a Triaxial Accelerometer. *Med. Sci. Sports Exerc.*, vol. 26, No. 12, pp. 151-1523, 1994.

Carlson et al., "Smart Prosthetics Based on Magnetorheological Fluids", 8th Annual Symposium on Smart Structures and Materials, Mar. 2001.

Carlson, J. David, What makes a Good MR Fluid?, 8th International Conference on Electrorheological (ER) Fluids and magnetorheological (MR) Suspensions, Nice 7 pages, Jul. 9-13, 2001.

Claiborne Jr., C.J., "Making Inodes Behave,", Linux Journal, Publ. By SSC Inc, USA, Feb. 2001, No. 82, pp. 94-99.

Copes/Bionic Ankle, The Most Significant Development in Ankle Prosthetics in Over a Half Century, 1985.

Crago, et al., New Control Strategies for Neuroprosthetic Systems, 1996.

Dai R, et al., Application of Tilt Sensors in Functional Electrical Stimulation. IEEE Trans. Rehab. Eng. 1996; 4(2):63-71.

Dietl, H. Bargehr, Der Einsatz von Elektronik bei Prothesen zur Versorgung der unteren Extremitat, Med. Orth. Tech. 117 1997, pp. 31-35.

Fisekovic, et al., New Controller for Functional Electrical Stimulation Systems, 2000.

Flowers, et al., Journal of Biomechanical Engineering: Transactions of the ASME; Feb. 1977, pp. 3-8.

Foerster, et al., Detection of Posture and Motion by Accelerometry—A Validation Study in Ambulatory Monitoring, 1999.

Foxlin, et al., Miniature 6-DOF Inertial System for Tracking HMDs, 1998.

Fujita, K. et al., Joint Angle Control with Command Filter for Human Ankle Movement Using Functional Electrical Stimulation, Proceed-

(56) References Cited

OTHER PUBLICATIONS ings of the 9th Annual Conference of the IEEE Engineering in Medicine and Biology Society, Nov. 13-16, 1987.
Gelat, Thierry et al., Adaptation of the gait initiation process for stepping on to a new level using a single step. Exp Brain Res(2000) 133-538-546, Jun. 21, 2000, pp. 9.
Graps, A., An Introduction to Wavelets, IEEE Computational Science & Engineering, 1995.
Grimes, Donald L., An Active Multi-Mode Above-Knee Prosthesis Controller, Massachusetts Institute of Technology 1979, 158 pages, 1979.
Gronqvist, Raoul et al., Human-centered approaches in slipperiness measurement, Ergonomics, Oct. 20, 2001, vol. 44, Issue 13, pp. 1167-1199 (32 pages).
Hanafusa et al., "A Robot Hand with Elastic Fingers and Its Application to Assembly Process," pp. 337-359, Robot Motion, Brady et al., MIT Press, Cambridge, MA, 1982.
Hanson, James P. et al., Predicting slips and falls considering required and available friction, Ergonomics, 1999, vol. 42, Issue 12, pp. 1619-1633 (15 pages).
Hashimoto et al., "An instrumented compliant wrist using a parallel mechanism," Japan/USA Symposium on Flexible Automation, vol. 1, pp. 741-744, ASME, 1992.
Hayes, W.C., et al., Leg Motion Analysis During Gait by Multiaxial Accelerometry: Theoretical Foundations and Preliminary Validations. *Journal of Biomechanical Engineering*, vol. 105, Aug. 1983, p. 283-289.
Herr, et al., "User-adaptive control of a magnetorheological prosthetic knee", Industrial Robot: an International Journal, vol. 30, No. 1, (2003) pp. 42-55.
Herr, Hugh, Presentation at "Experiencing the Frontiers of Biomedical Technology," (Mar. 10-11, 2003).
Herr, et al., Patient-Adaptive Prosthetic and Orthotic Leg Systems, 12th nordic Baltic Conference on Biomedical Engineering and Medical Physics, Processdings of the International Federation for medical & Biological Engineering, 2002.
Heyn, Andreas, et al., The Kinematics of the Swing Phase Obtained From Accelerometer and Gyroscope Measurements, *18th Annual International Conference of the IEEE Engineering in Medicine and Biology Society*, Amsterdam 1996, p. 463-464.
Hill, Stephen W. et al., Altered kinetic strategy for the control of swing limb elevation over obstacles in unilateral below-knee amputee gait, Journal of Biomechanics, 1999, vol. 32, pp. 545-549 (5 pages).
Howard, "Joint and Actuator Design for Enhanced Stability in Robotic Force Control," Ph.D. thesis, Massachusetts Inst. of Technology, Dept. of Aeronautics and Astronautics, 1990.
Jonic, et al., Three Machine Learning Techniques for Automatic Determination of Rules to Control Locomotion, 1999.
Kidder, Steven M., et al., A System for the Analysis of Foot and Ankle Kinematics During Gait. *EEE Transactions on Rehabilitation Engineering*, vol. 4, No. 1, Mar. 1996.
Kirkwood, et al., Automatic Detection of Gait Events: A Case Study Using Inductive Learning Techniques, 1989.
Kirsner, Scott, "A Step in the Right Direction Biomedical Horizons Expanding," Boston Globe (Mar. 17, 2003).
Kooij, et al., A Multisensory Integration Model of Human Stance Control, 1998.
Kostov, et al., Machine Learning in Control of Functional Electrical Stimulation Systems for Locomotion, 1995.
Kuster, M., et al., Kinematic and kinetic comparison of downhill and level walking, Clinical Biomechanics, 1995, vol. 10, Issue 2, pp. 79-84 (6 pages).
LaFortune, Mario A., Three Dimensional Acceleration of the Tibia During Walking and Running. *J. Biomechanics* vol. 24, No. 10, pp. 877-886, 1991.
Lee, S., Activity and Location Recognition Using Wearable Sensors, Pervasive Computing, IEEE, 2002.
LeFebvre, W., "Permissions and Access Control Lists", UNIX Review's Performance Computing, Publ. by Miller Freeman, USA, Oct. 1998, vol. 16, No. 11, pp. 59-61.
Light, L.H., et al., Skeletal Transients on Heel Strike in Normal Walking with Different Footwear, Biomechanics, vol. 13, 1980, pp. 477-480.
Luinge, H.J., Inertial Sensing of Movement. Doctoral Thesis, Twente University Press, Enschede, Netherlands (2002) p. 9-13.
Mayagoitia, Ruth E., et al., Accelerometer and Rate Gyroscope Measurement of Kinematics: An Inexpensive Alternative to Optical Motion Analysis Systems. *Journal of Biomechanics* 35 (2002) 537-542.
Moe-Nilssen, A New Method for Evaluating Motor Control in Gait Under Real-Life Environmental Conditions, Parts 1—The instrument; Part 2: Gait Analysis, 1997.
Morris, J.R. W., Accelerometry—A Technique for the Measurement of Human Body Movements, *J. Biomechanis*, 1973, vol. 6, pp. 729-736.
Moseley, Anne M. et al., High- and low-ankle flexibility and motor task performance, Gait and Posture, 2003, vol. 18, pp. 73-80 (8 pages).
Nadeau, S. et al., Frontal and sagittal plane analyses of the stair climbing task in healthy adults aged over 40 years: what are the challenges compared to level walking?, Clinical Biomechanics, 2003, vol. 18, pp. 950-959 (10 pages).
A. Nakagawa, Intelligent Knee Mechanism and the Possibility to Apply the Principle to the Other Joints, Engineering in Medicine and Biology Society, Proceedings of the 20th Annual International Conference of the IEEE, vol. 20, No. 5, Dec. 1998, at 2282.
Namespaces in XML, World Wide Web Consortium Working Draft Sep. 16, 1998; Tim bray (Textuality); Dave Hollander (Hewlett-Packard Company); Andrew Layman (Microsoft).
Otto Bock Orthopadische Industrie, C-LEG a new dimension in amputee mobility, Otto Bock Data Sheet 1997.
Otto Bock Orthopadische Industrie GMBH & Co., C-Leg Fitting Statistics (Abstract), Mar. 2000, 4 pages.
Otto Bock Orthopadische Industrie, The Electronic C-Leg compact Leg Prosthesis System, Instructions for Use; 2002.
Otto Bock Orthopadische Industrie, The Electronic C-Leg Knee Joint System, Instructions for Use; 2002. available at http://www.ottobockus.com/products/lower_limb_prosthetics/c-leg_instructions.pdf, 32 pages (printed Jul. 20, 2006).
Otto, Judith, "Prosthetic Knees: What's on the Way?", The O&P edge, http://www.oandp.com/edge/issues/ articles/2003 -10_02 .asp, Oct. 2003, 5 pages.
Otto, Judith, "Prosthetic Knees: What's Currently New and Impressive?", The O&P Edge, http://www.oandp.com/edge/issues/articles/2003-10_03.sp, Oct. 2003, 4 pages.
Petrofsky, Jerrold S., et. al., Feedback Control System for Walking in Man. *Comput. Biol. Med.* vol. 14, No. 2, pp. 135-149, 1984.
Pfeffer et al. , "Experiments with a Dual-Armed, Cooperative, Flexible-Drivetrain Robot System," Proc. 1993 IEEE Int. Conf. on Robotics & Automation, vol. 3, pp. 601-608, May 5, 1993.
Popovic, D. et al.; Optimal control for an Above-Knee Prosthesis With Two Degrees of Freedom, 1995, pp. 89-98, Jo. Biomechanics, vol. 28, No. 1.
Dejan Popovic et al., Control Aspects of Active Above-Knee Prosthesis, International Journal of Man-Machine Studies, vol. 35, Issue 6, Dec. 1991, at 751.
Powers, Christopher M. et al., Stair ambulation in persons with transtibial amputation: An analysis of the Seattle LightFootTM, Journal of Rehabilitation Research and Development, Jan. 1997, vol. 34, Issue 1, pp. 9-18 (10 pages).
Rao, Sreesha S. et al., Segment Velocities in Normal and Transtibial Amputees: Prosthetic Design Implications, IEEE Transactions on Rehabilitation Engineering, Jun. 1998, vol. 6, Issue 2, pp. 219-226 (8 pages).
Redfern, Mark S. et al., Biomechanics of descending ramps, Gait and Posture, 1997, vol. 6, pp. 119-125 (7 pages).
Reiner, Robert et al., Stair ascent and descent at different inclinations, Gait and Posture, 2002, vol. 15, pp. 32-44 (13 pages).

(56) References Cited

OTHER PUBLICATIONS

Reitman, J. S., et al., Gait Analysis in Prosthetics: Opinions, Ideas, and Conclusions, Prosthetics and Orthotics International, 2002, 26, 50-57.
Robinson, David W. et al., *Series Elastic Actuator Development for a Biomimetic Walking Robot*, MIT Leg Laboratory, 1999.
Robinson, David William, *Design and Analysis of Series Elasticity in Closed-Loop Actuator Force Control*, MIT Department of Mechanical Engineering, Jun. 1996.
Schmalz T. et al., "Energy Efficiency of Trans-Femoral Amputees Walking on Computer-Controlled Prosthetic Knee Joint 'C-LEG'" in 3 pages, International Society for Prosthetics and Orthotics: Conference book IXth World Congress ISPO, 1998.
Sekine, et al., Classification of Waist-Acceleration Signals in a Continuous Walking Record, 2000.
Sin S. W., et al., Significance of Non-Level Walking on Transtibial Prosthesis Fitting with Particular Reference to the Effects of Anterior-Posterior Alignment, Journal of Rehabilitation Research and Development vol. 38 No. 1, Jan./Feb. 2001, p. 1-6.
Smidt, G.L., et al., An Automated Accelerometry System for Gait Analysis, *J. Biomechanics.* 1977, vol. 10, pp. 367-375.
State-of-the-Art Prosthetic Leg Incorporates Magneto-Rheological Technology, Medical Product Manufacturing News, p. 42, Nov. 2000.
Suga, T, et al., "Newly designed computer controlled knee-ankle-foot orthosis (Intellegent Orthosis)", Prostetics and Orthotics International, 1998, 22, 230-239.
Sugano et al., "Force Control of the Robot Finger Joint equipped with Mechanical Compliance Adjuster," Proc. 1992 IEEE/RSJ Int. Conf. on Intell. Robots & Sys., pp. 2005-2013, Jul. 1992.
Thakkar, Sneha, "Energy Economy Gait Analysis of an Autoadaptive Prosthetic Knee", Master's Thesis submitted to the Dept. of Electrical Engineering and Computer Science, MIT (2002) pp. 1-58.
R. Tomovic et al., *A Finite State Approach to the Synthesis of Bioengineering Control Systems*, IEEE Transactions on Human Factors in Electronics, vol. HFE-7, No. 2, Jun. 1966.
Tong, et al., Virtual Artificial Sensor Technique for Functional Electrical Stimulation, 1998.
Tong, Kaiyu and Malcolm H. Granat, *A Practical Gait Analysis System Using Gyroscopes*, Medical Engineering & Physics, vol. 21, No. 2, Mar. 1999, at 87-94.
Townsend Ma et al., "Biomechanics and modeling of bipedal climbing and descending." Journal of Biomechanics 1976, vol. 9, No. 4, pp. 227-239, XP008078405.
U.S. Appl. No. 60/371,974 to Martin, filed Apr. 12, 2002.
Van der Loos, H.F.M., et al., "ProVAR Assistive Robot System Architecture", Proceedings of the 1999 IEEE International Conference on Robotics & Automation; Detroit, Michigan, May 1999, pp. 741-746.
Peter H. Veltink et al. (1993), The Feasibility of Posture and Movement Detection by Accelerometry, in 15th Annual International Conference of the IEEE Engineering in Medicine and Biology Society, Oct. 28-31, 1993, San Diego, CA, 1230-1231.
Veltink, et al., Detection of Static and Dynamic Activities Using Uniaxial Accelerometers, 1996.
Wilkenfeld, Ari Ph.D.; An Auto-Adaptive External Knee Prosthesis, Artificial Intelligence Laboratory, MIT, Cambridge, Massachusetts, 3 pages, Sep. 2000.
Wilkenfeld, Ari Ph.D.; Biologically inspired autoadaptive control of a knee prosthesis, Dissertation Abstract, MIT, Cambridge, Massachusetts, 1 page, Sep. 2000.
Willemsen, A. Th. M., et al., Real-Time Gait Assessment Utilizing a New Way of Accelerometry. *J. Biomechanics* vol. 23, No. 8, pp. 859-863, 1990.
Willemsen, Antoon Th. M., et al., Automatic Stance-Swing Phase Detection from Accelerometer Data for Peroneal Nerve Stimulation. *IEEE Trasnactions on Biomedical Engineering*, vol. 37, No. 12, Dec. 1990, p. 1201-1208.
Williamson, Matthew M., *Series Elastic Actuators*, Massachusetts Institute of Technology Artificial Intelligence Laboratory, A.I. Technical Report No. 1524, Jan. 1995.
Woodward, M I, et al., Skeletal Accelerations Measured During Different Exercises. *Proceedings of the Institution of Mechanical Engineers*, Part H: Journal of Engineering Medicine 1993 207:79, DOI: 10.1243/PIME_PROC_1993_207_274_02.
Wu, Ge, The Study of Kinematic Transients in Locomotion Using the Integrated Kinematic Sensor, IEEE Transactions on Rehabilitation Engineering, vol. 4, No. 3, Sep. 1996, p. 193-200.
Flowers, A Man-Interactive Simulator System for Above-Knee Prosthetics Studies, Aug. 1972.
Martens, W.L.J.; "Exploring Information Content and Some Application of Body Mounted Piezo-Resistive Accelerometers," In P.H. Veltink, & R.C. van Lummel (Eds.), Dynamic analysis using body fixed sensors, Second World Congress of Biomechanics, Amsterdam, 1994, pp. 9-12.
Murray, M. Pat, et al. Walking Patterns of Normal Men, The Journal of Bone and Joint Surgery, vol. 46-A, No. 2, Mar. 1964.
Otto Bock's C-Leg, see http://web.archive.org/web/20040215152410/http:/www.ottobockus.com/products/lower_limb_prosthetics/c-leg.asp. Believed to have been available more than one year before Nov. 18, 2003. Applicant requests the Examiner to consider this reference as qualifying as prior art to the present application, but reserves the right to challenge the reference's prior art status at a later date.
Perry, Jacquelin, MD, Gait Analysis: Normal and Pathological Function, 1992.
Sowell, T.T., A Preliminary Clinical Evaluation of the Mauch Hydraulic Foot-Ankle System, 5 Prosthetics and Orthotics International 87 (1981).

\* cited by examiner

INSTRUMENTED PROSTHETIC FOOT

CROSS-REFERENCE TO RELATED APPLICATIONS

The present application is a continuation of U.S. patent application Ser. No. 11/881,964, filed 31 Jul. 2007, and entitled "INSTRUMENTED PROSTHETIC FOOT", which is a divisional application of U.S. patent application Ser. No. 10/715,989, filed 18 Nov. 2003, each of which is incorporated herein by reference in its entirety and is to be considered a part of this specification.

BACKGROUND

1. Field

The present invention relates to a prosthetic foot for use with a control system and/or a method for controlling an actuated leg prosthesis.

2. Background

As is well known to control engineers, the automation of complex mechanical systems is not something easy to achieve. Among such systems, conventional powered artificial limbs are notorious for having control problems. These conventional prostheses are equipped with basic controllers that artificially mobilize the joints without any interaction from the amputee and are only capable of generating basic motions. Such basic controllers do not take into consideration the dynamic conditions of the working environment, regardless the fact that the prosthesis is required to generate appropriate control within a practical application. They are generally lacking in predictive control strategies necessary to anticipate the artificial limb's response as well as lacking in adaptive regulation enabling the adjustment of the control parameters to the dynamics of the prosthesis. Because human limb mobility is a complex process including voluntary, reflex and random events at the same time, conventional prostheses do not have the capability to interact simultaneously with the human body and the external environment in order to have minimal appropriate functioning.

Accordingly, it is an object of the present application to obviate or mitigate some or all of the above disadvantages.

SUMMARY

According to the present invention, there is provided an instrumented prosthetic foot for use with an actuated leg prosthesis controlled by a controller, the instrumented prosthetic foot comprising a connector to connect the instrumented prosthetic foot to the leg prosthesis, an ankle structure connected to the connector, a ground engaging member connected to the ankle, at least one sensor for detecting changes in weight distribution along the foot, and an interface for transmitting signals from the sensor to the controller.

BRIEF DESCRIPTION OF THE DRAWINGS

Embodiments of the invention will be described by way of example only with reference to the accompanying drawings, in which.

DETAILED DESCRIPTION

The appended figures show a instrumented prosthetic foot (20) having sensors (22A, 22B) for use, in cooperation with possible additional sensors (24A, 24B, 26), with a control system (100) for controlling a prosthesis (14) having an actuating mechanism (16). It should be understood that the present invention is not limited to the illustrated implementation since various changes and modifications may be effected herein without departing from the scope of the appended claims.

Figure 1:
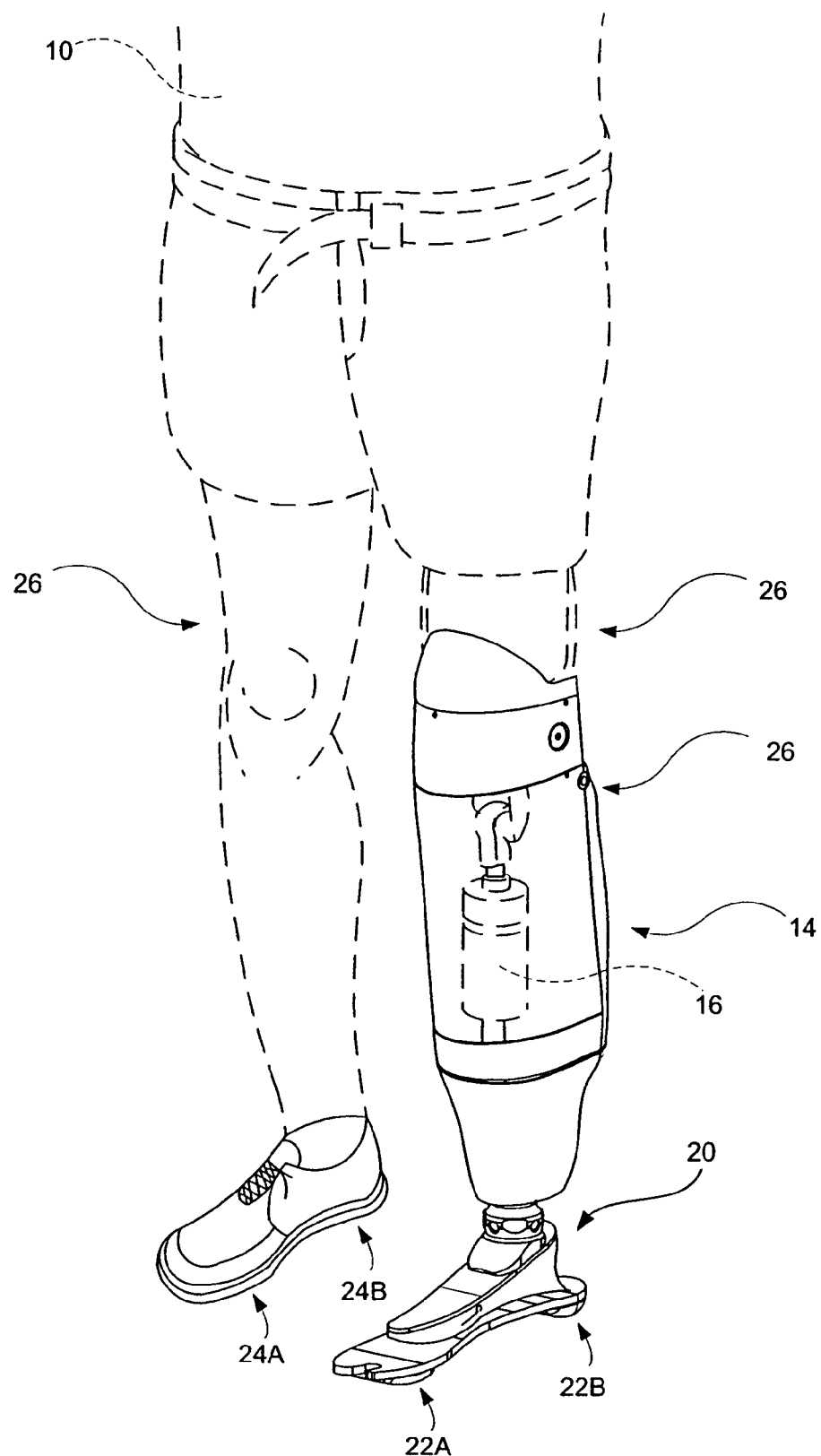
FIG. 1 shows the lower body of an individual provided with a prosthesis and an instrumented prosthetic foot on one side and having a healthy leg on the other side

Referring therefore to FIG. 1 an individual (10) has a pair of legs (26) and (28), one of which, (26), is amputated above the knee. A prosthesis (14) is attached to the leg (26) and includes an actuating mechanism (16), which may be either passive or active. An instrumented prosthetic foot (20) is attached to the prosthesis (14) and includes sensors (22A, 22B). Additional sensors (24A, 24B) are located on the healthy foot and additional sensors (26) located on the individual (10) and/or the prosthesis (14). A passive actuating mechanism may be generally defined as an electromechanical component that only absorbs mechanical energy in order to modify dynamics of mechanical joints of the prosthesis, while an active actuating mechanism may be generally defined as an electromechanical component that absorbs and supplies mechanical energy in order to set dynamics of mechanical joints of the prosthesis.

An example of a passive actuating mechanism is described in U.S. patent application Ser. No. 09/767,367, filed Jan. 22, 2001, entitled "ELECTRONICALLY CONTROLLED PROSTHETIC KNEE". Examples of active actuating mechanisms are described in U.S. patent application Ser. No. 10/463,495 filed Jun. 17, 2003, entitled "ACTUATED PROSTHESIS FOR ABOVE-KNEE AMPUTEES", by Stephane Bedard et al., the entire disclosure of which is hereby incorporated by reference herein.

Figure 2:
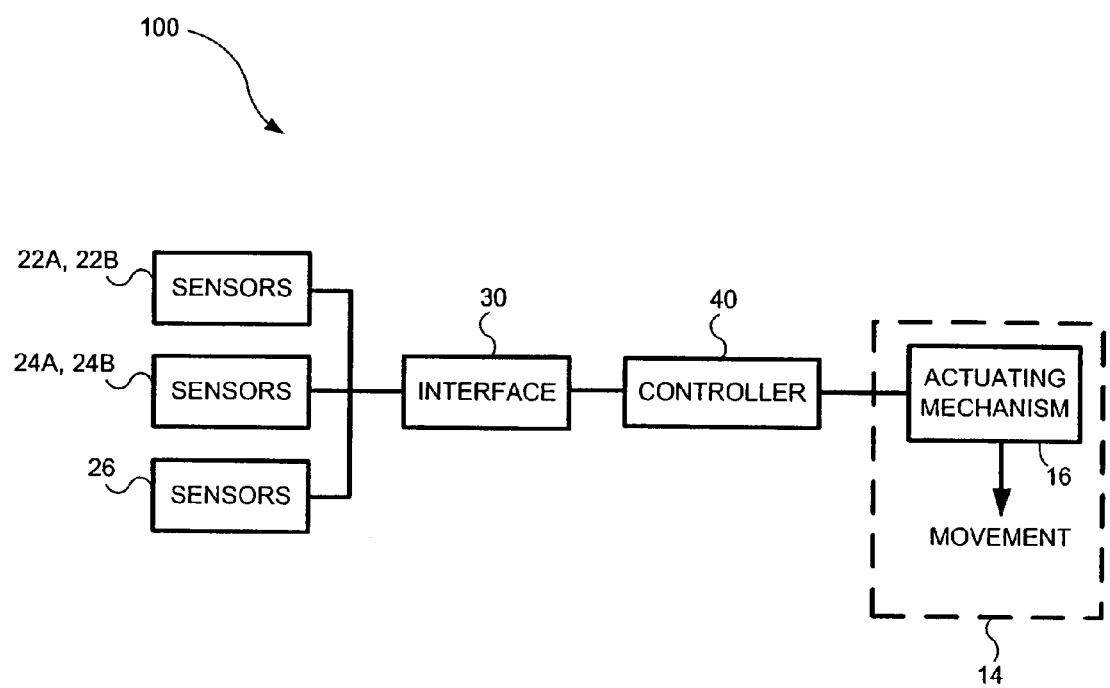
FIG. 2 is a block diagram showing a control system for a prosthesis having an actuating mechanism.

The prosthesis (14) is controlled, as shown schematically in FIG. 2, by a basic control system (100) comprising sensors (22A, 22B, 24A, 24B, 26), connected through an interface (30) to a controller (40). The controller (40) provides signals to an actuating mechanism (16) in the prosthesis (14), such as shown in FIG. 1. The purpose of the control system (100) is to provide the required signals for controlling the actuating mechanism (16). To do so, the control system (100) is interfaced with the amputee (10) using sensors (22A, 22B, 24A, 24B, 26) to ensure proper coordination between the amputee (10) and the movements of the prosthesis (14). The sensors (22A, 22B, 24A, 24B, 26) capture information, in real time, about the dynamics of the amputee's movement and provide that information to the controller (40) via the interface (30). The controller (40) then uses the information to determine the resistance to be applied to a joint, in the case of a passive actuating mechanism, or the joint trajectories and the required angular force or torque that must be applied by a joint, in the case of an active actuating mechanism, in order to provide coordinated movements.

The sensors (22A, 22B, 24A, 24B, 26) may include myoelectric sensors, neuro-sensors, kinematic sensors, kinetic sensors, strain gauges or plantar pressure sensors. Myoelectric sensors are electrodes used to measure the internal or the external myoelectrical activity of skeletal muscles. Neuro-sensors are electrodes used to measure the summation of one or more action potentials of peripheral nerves. Kinematic sensors are used to measure the position of articulated joints, the mobility speed or acceleration of lower extremities. Kinetic sensors are used to measure angular forces at articulated joints or reaction forces of lower extremities. Strain gages are used to measure the strain forces at a specific underfoot area. Plantar pressure sensors are used to measure the vertical plantar pressure of a specific underfoot area. Of course, additional types of sensors which provide various information about dynamics of human locomotion may be used. For a given application, the use of sensors (22A, 22B, 24A, 24B, 26) is not restricted to a specific type of sensor, multiple types of sensors in various combinations may be used.

As illustrated in FIG. 1, the sensors (22A, 22B) may comprise localized plantar pressure sensors located at spaced locations on the prosthetic foot (20) to measure the vertical plantar pressure of a specific underfoot area. Similarly, the plantar pressure sensors (24A, 24B) located on the side of the healthy foot may be provided at spaced locations in a custom-made insole, preferably in the form of a standard orthopaedic insole, that is modified to embed the two sensors (24A, 24B) for the measurement of two localized plantar pressures. The sensors (22A, 22B, 24A, 24B) are operable to measure the weight transfer along the foot as the individual moves which may be combined with other sensors (26) such as kinematic sensors to measure the angular speed of body segments of the lower extremities and kinematic sensors to measure the angle of the prosthesis (14) knee joint.

Each sensor (22A, 22B, 24A, 24B) may comprise a thin Force-Sensing Resistor (FSR) polymer cell directly connected to the interface (30) of the control system (100) or indirectly using an intermediary system (not shown), for instance a wireless emitter. Of course, other types of communication link technologies may be used, such as, for example, optical. The FSR cell has a decreasing electrical resistance in response to an increasing force applied perpendicularly to the surface thereof. Each cell outputs a time variable electrical signal for which the intensity is proportional to the total vertical plantar pressure over its surface area. The size and position of the plantar pressure sensors (22A, 22B, 24A, 24B) may be defined in accordance with the stability and the richness (intensity) of the localized plantar pressure signals provided by certain underfoot areas during locomotion. For example, it was found by experimentation that the heel and the toe regions are two regions of the foot sole where the Plantar Pressure Maximum Variation (PPMV) may be considered as providing a signal that is both stable and rich in information.

Accordingly, the controller (40) may use the data signals from the four localized plantar pressure sensors (22A, 22B, 24A, 24B), as well as the information gathered from the data signals of the other sensors (26) such as kinematic sensors, in order to decompose the locomotion of the individual (10) into a finite number of states, and generate the appropriate control signals for controlling the actuating mechanism (16) according to the locomotion. Of course, the controller (40) is not limited to the use of the preceding data signals.

An example of a controller (40) and control system (100) using sensors comprising plantar pressure sensors as well as kinematic sensors is described in U.S. patent application Ser. No. 10/600,725 filed Jun. 20, 2003, entitled "CONTROL SYSTEM AND METHOD FOR CONTROLLING AN ACTUATED PROSTHESIS", by Stephane Bedard, the entire disclosure of which is hereby incorporated by reference herein.

Figure 3:
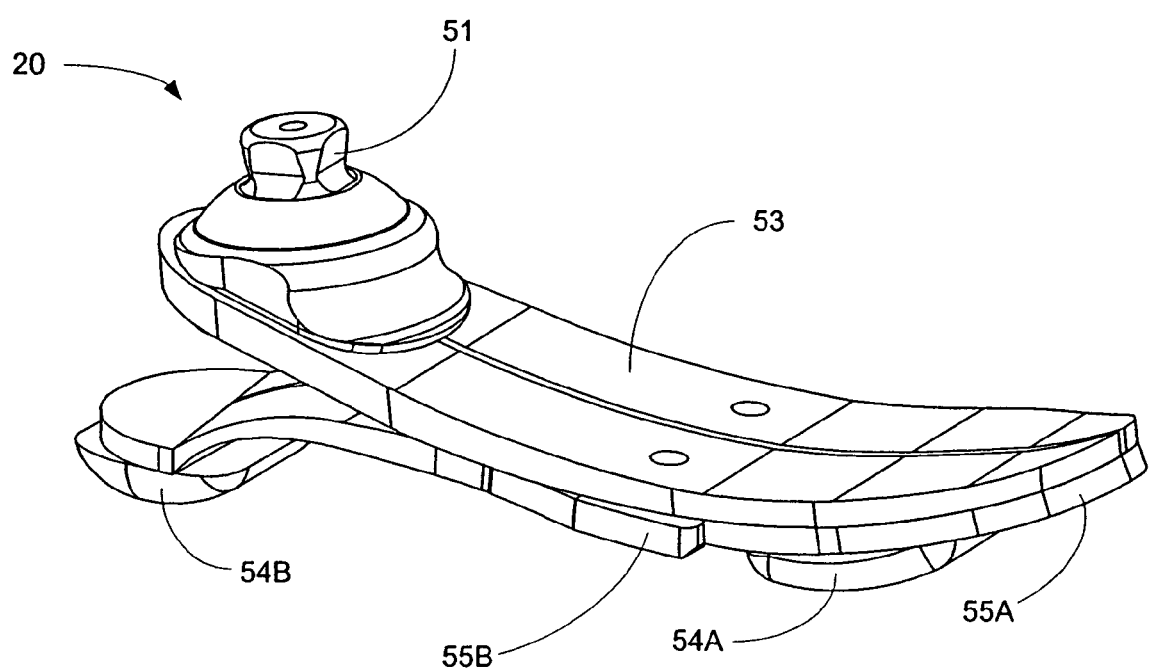
FIG. 3 is a perspective view, from the front and slightly above, of a instrumented prosthetic foot.
Figure 4:
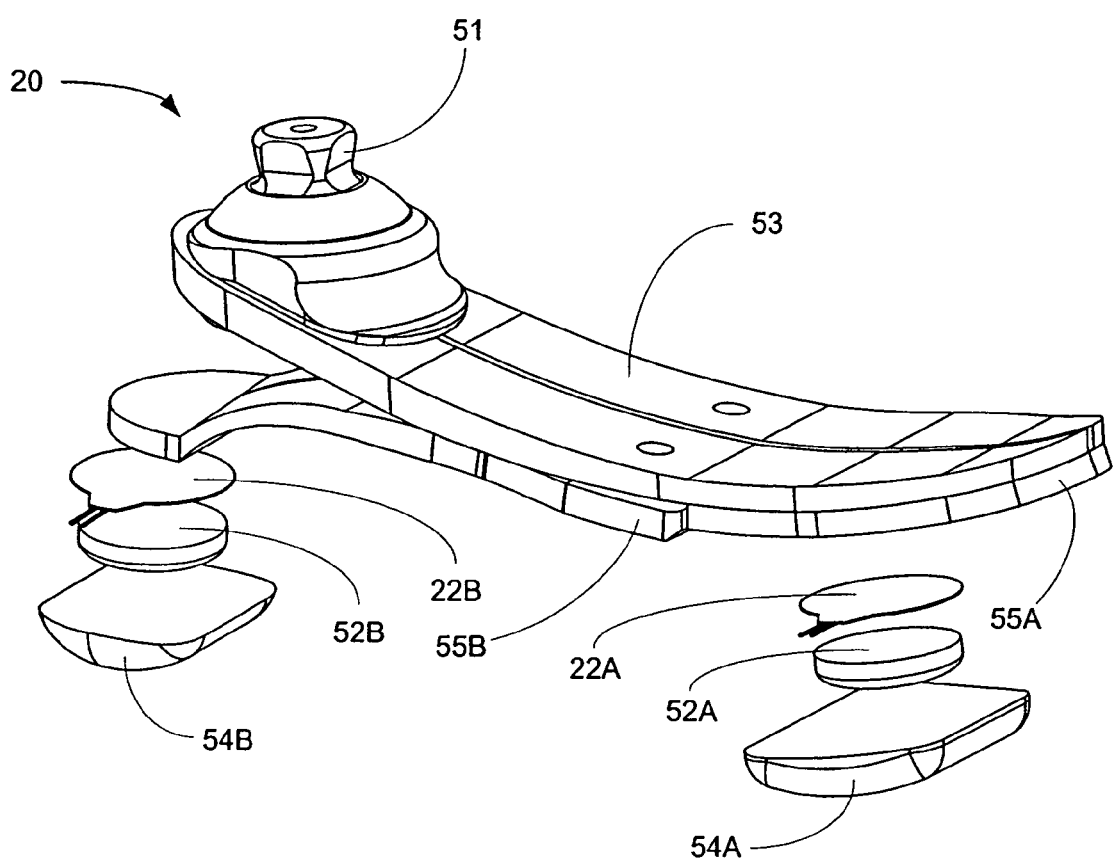
FIG. 4 is an exploded perspective view of the instrumented prosthetic foot of FIG. 3.

To facilitate the acquisition of the data in a repeatable and dependable manner, the sensors (22A, 22B) are incorporated in to the structure of the foot (20). An embodiment of the instrumented prosthetic foot (20) is shown in more detail in FIGS. 3 and 4. The instrumented prosthetic foot (20) includes a foot plate (53), forming an elongated body, with a connector (51) at one end, a toe plate (55A) and a heel plate (55B) that is cantilevered from the foot plate (53). Such an arrangement is provided by, for example, a Vari-Flex® prosthetic foot from Össur. Pressure sensors (22A, 22B) are located at longitudinally spaced locations on the underside of the foot plate (53) and heel plate (55) respectively. The sensors (22A, 22B) are covered by rigid plates (52A, 52B) and resilient pads (54A, 54B). The pressure sensors (22A, 22B) are located so as to be responsive to loads imposed on the instrumented prosthetic foot (20) at the regions corresponding to the toe area and the heel area respectively.

The rigid plates (52A, 52B) covering the sensors (22A, 22B), although not essential, help to optimize the pressure distribution on the entire surface of the sensors (22A, 22B) as well as inhibiting any shearing and may be made of 85 A durometer polyurethane. Of course, other type of material may be used as well.

The pads (54A, 54B) wrap up the rigid plates (52A, 52B) and the sensors (22A, 22B), forming a ground engaging member, in order to optimize the contact between the instrumented prosthetic foot (20) and the ground. The pads (54A, 54B) may be made of 40 A durometer polyurethane. Of course, other type of material may be used as well.

In operation, therefore, as the foot (20) traverses the ground, the force applied to the heel plate (55B) is measured by the sensor (22B) and a corresponding signal forwarded to the controller (40). The force applied to the toe plate (55A) is also measured by the sensor (22A) and the relative loading between the two locations is measured. As the foot (20) continues to traverse the ground, the force applied to the toe area increases and that at the heel decreases to provide a pair of signals from which the disposition of the leg may be determined and the appropriate control provided to the actuator (16).

Figure 5:
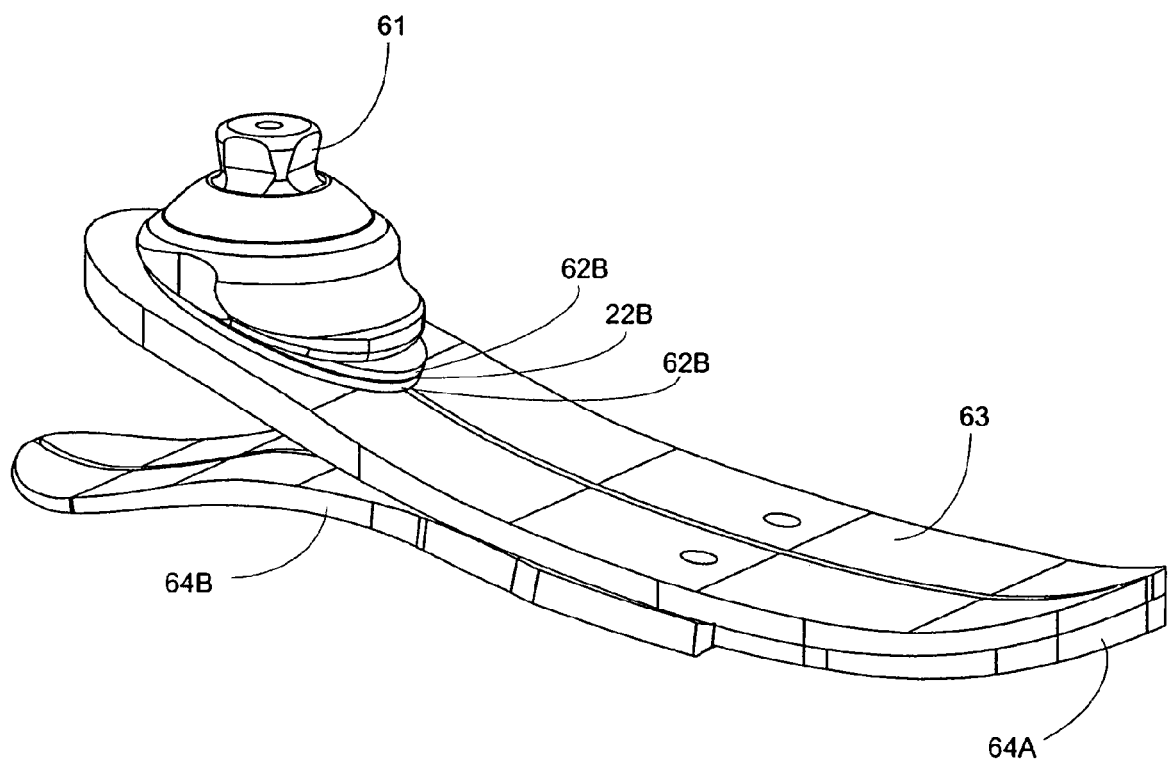
FIG. 5 is a perspective view, from the front and slightly above, of an alternative embodiment of the instrumented prosthetic foot of FIG. 3.
Figure 6:
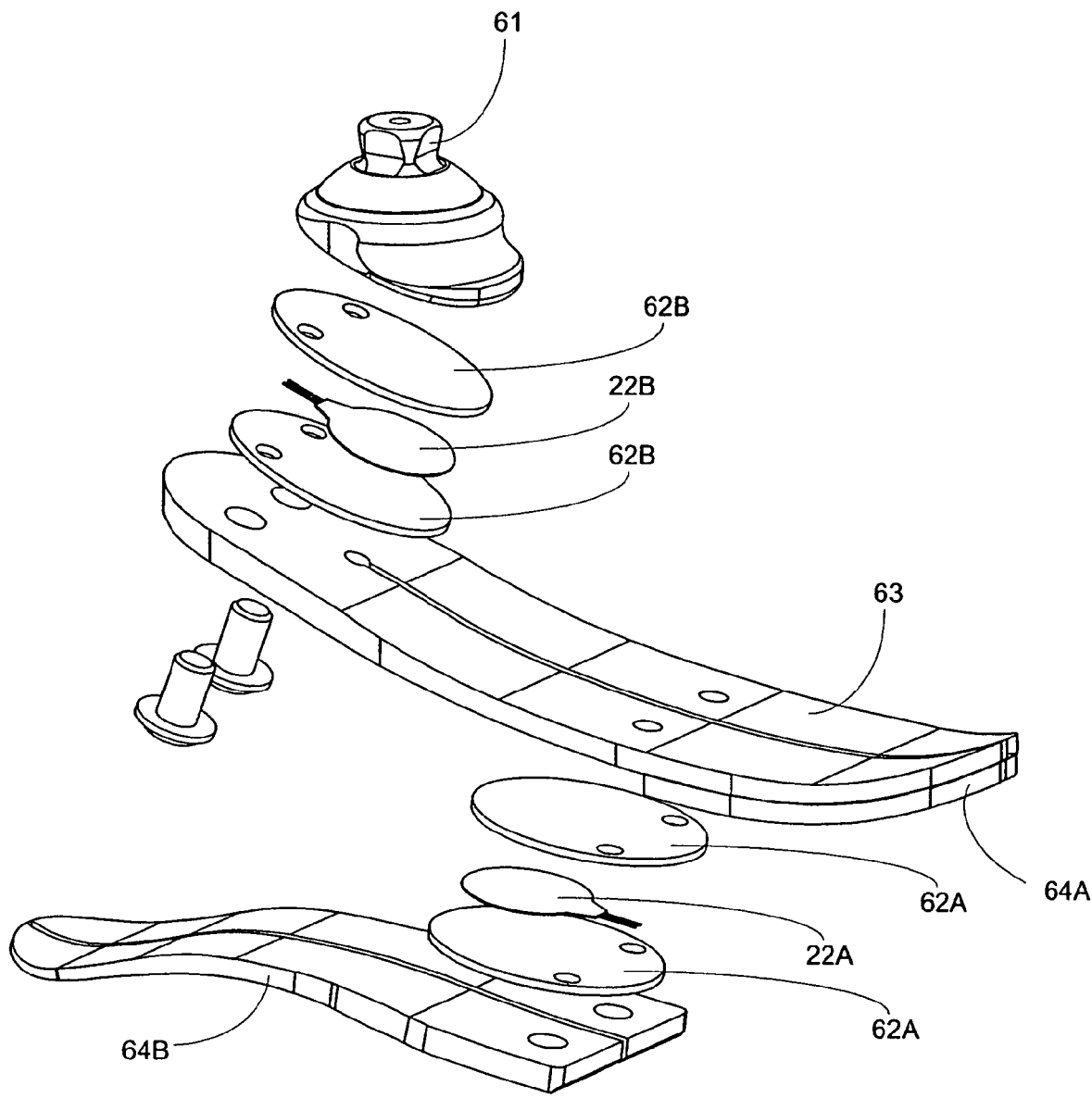
FIG. 6 is an exploded perspective view of the instrumented prosthetic foot of FIG. 5.

An alternative embodiment of the instrumented prosthetic foot (20) is shown in FIGS. 5 and 6. The instrumented prosthetic foot (20) includes connector (61), foot plate (63), toe plate (64A) and heel plate (64B), such as provided by, for example, a Vari-Flex® prosthetic foot from Össur. Pressure sensors (22A, 22B) are located between the foot plate (63) and rigid plates (62A, 62B). The pressure sensors (22A, 22B) are located so as to be responsive to load imposed on the instrumented prosthetic foot (20) at the regions corresponding to the toe area and the heel area respectively. More specifically, pressure sensor (22A) is sandwiched between a pair of rigid plates (62A), which in turn are positioned between the heel plate (64B) and the foot plate (63). Pressure sensor (22B) is sandwiched between a pair of rigid plates (62B), which in turn are positioned between the foot plate (63) and the connector (61).

As for the previous embodiment, rigid plates (62A, 62B) covering the sensors (22A, 22B), although not essential, help to optimize the pressure distribution on the entire surface of the sensors (22A, 22B) as well as inhibiting any shearing and may be made of 85 A durometer polyurethane. Of course, other type of material may be used as well.

Figure 7:
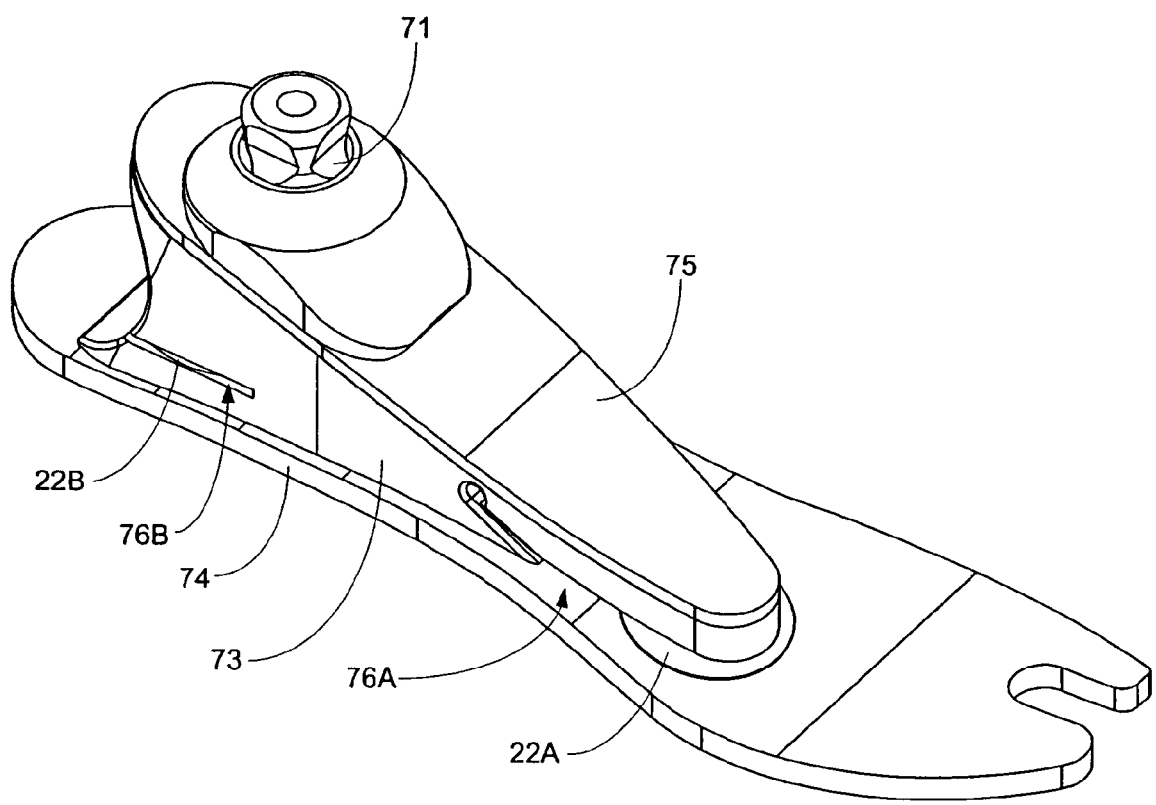
FIG. 7 is a perspective view, from the front and slightly above, of another alternative embodiment of the instrumented prosthetic foot of FIG. 3
Figure 8:
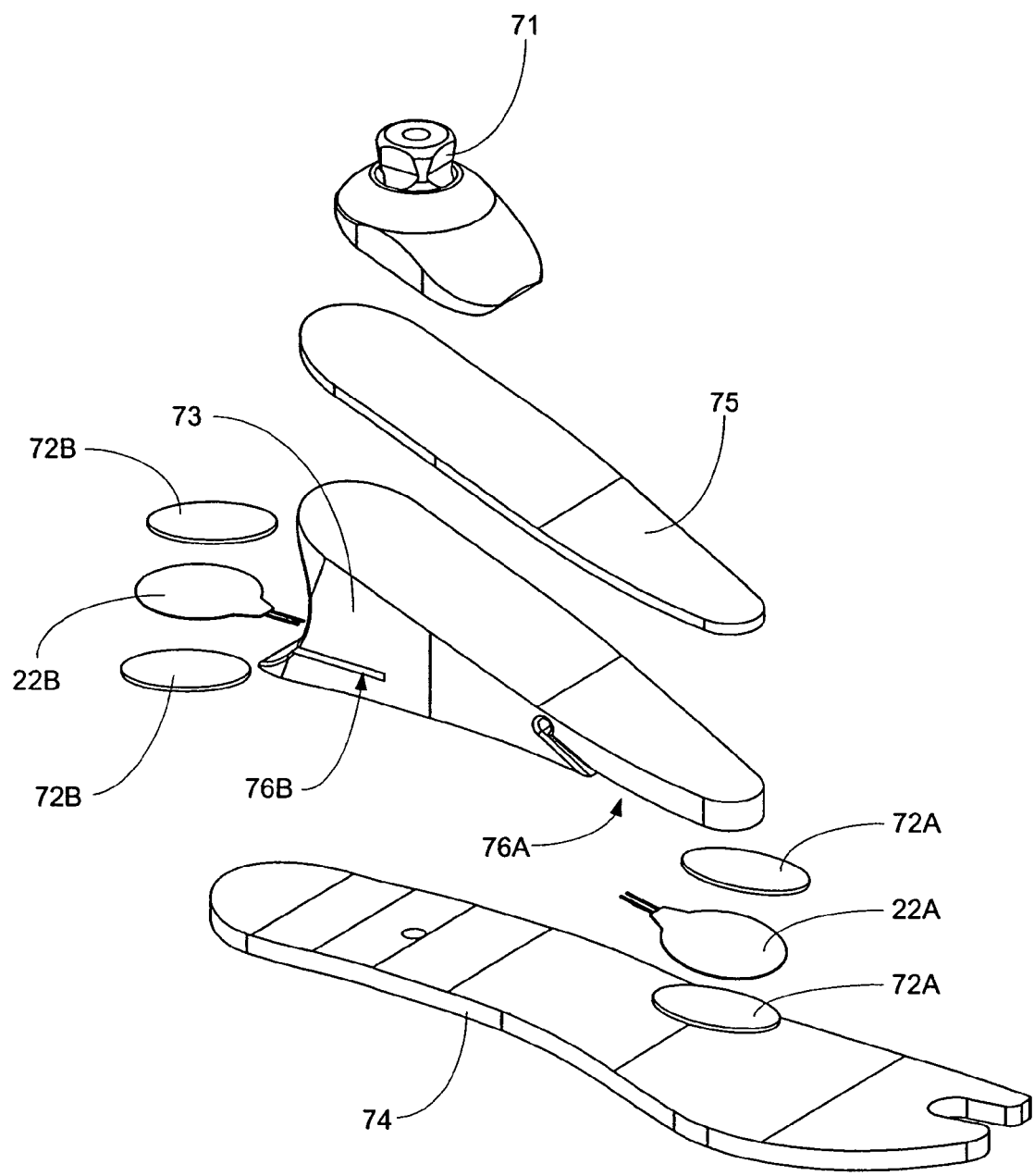
FIG. 8 is an exploded perspective view of the instrumented prosthetic foot of FIG. 7.

Another alternative embodiment of the instrumented prosthetic foot (20) is shown in FIGS. 7 and 8. The instrumented prosthetic foot (20) includes connector (71), top foot plate (75), foam cushion core (73) and bottom foot plate (74), such as provided by, for example, a LP Talux® prosthetic foot from Össur. Pressure sensors (22A, 22B) are sandwiched between pairs of rigid plates (72A, 72B). The pressure sensors (22A, 22B) are located so as to be responsive to load imposed on the instrumented prosthetic foot (20) at the regions corresponding to the toe area and the heel area respectively. More specifically, pressure sensor (22A) is sandwiched between a pair of rigid plates (72A), which in turn are positioned within gap (76A), which is located between a bottom foot plate (74) and a foam cushion core (73). Pressure sensor (22B) is sandwiched between a pair of rigid plates (72B), which in turn are positioned within gap (76B), which is located within the foam cushion core (73).

Again, as for the previous embodiments, rigid plates (72A, 72B) covering the sensors (22A, 22B), although not essential, help to optimize the pressure distribution on the entire surface of the sensors (22A, 22B) as well as preventing any shearing and may be made of 85 A durometer polyurethane. Of course, other type of material may be used as well.

Figure 9:
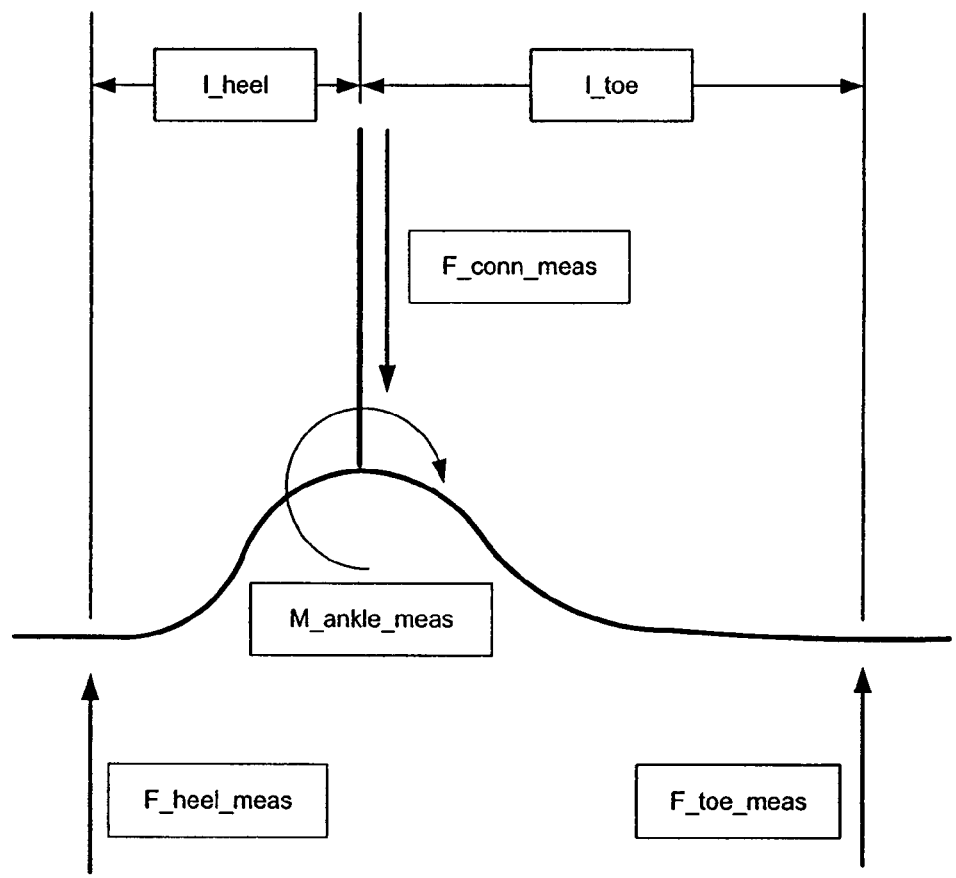
FIG. 9 is schematic view of forces exerted on a foot.

In the previous embodiments, the force (or pressure) at the toe and heel areas, F_toe and F_heel respectively, was obtained by positioning pressure sensors (22A, 22B) directly at those areas. More specifically, referring to FIG. 9, F_toe and F_heel were obtained as follows:

$$F\_toe = F\_toe\_meas \quad \text{Equation 1}$$

$$F\_heel = F\_heel\_meas \quad \text{Equation 2}$$

In other possible embodiments of the instrumented prosthetic foot (20), sensors (22A, 22B) may not be restricted to being positioned directly at the toe and heel areas, the equivalent information may be obtained by measuring the equivalent torque at the ankle and the axial force at the connector of the instrumented prosthetic foot (20). F_toe and F_heel may be defined in terms of the torque measured at the ankle, M_ankle_meas, and the force measured at the connector, F_conn_meas, using the following equations:

$$F\_toe = \frac{M\_ankle\_meas + (F\_conn\_meas \cdot I\_heel)}{(I\_heel + I\_toe)} \quad \text{Equation 3}$$

$$F\_heel = \frac{-M\_ankle\_meas + (F\_conn\_meas \cdot I\_toe)}{(I\_heel + I\_toe)} \quad \text{Equation 4}$$

where
I_heel is the distance between the center of the connector and the center of the heel area;
I_toe is the distance between the center of the connector and the center of the toe area.

Figure 10:
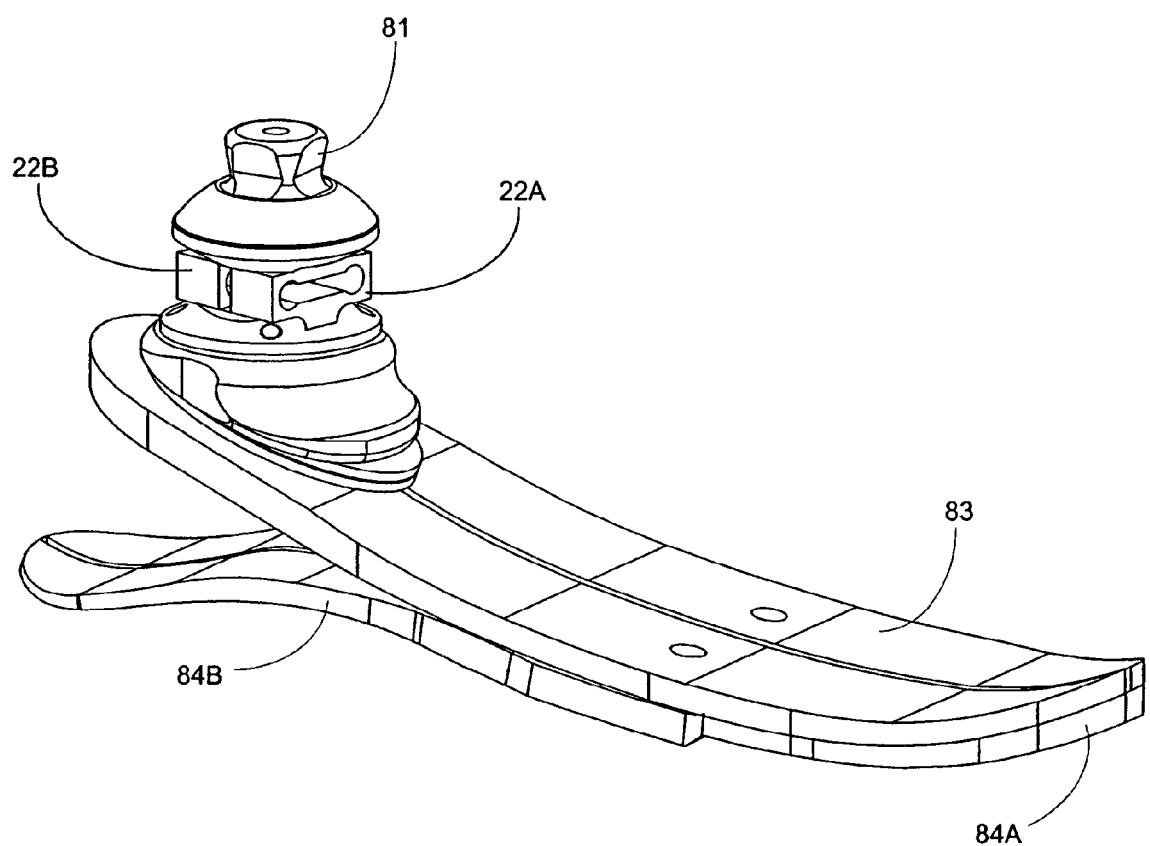
FIG. 10 is a perspective view, from the front and slightly above, of a further still alternative embodiment of the instrumented prosthetic foot of FIG. 3
Figure 11:
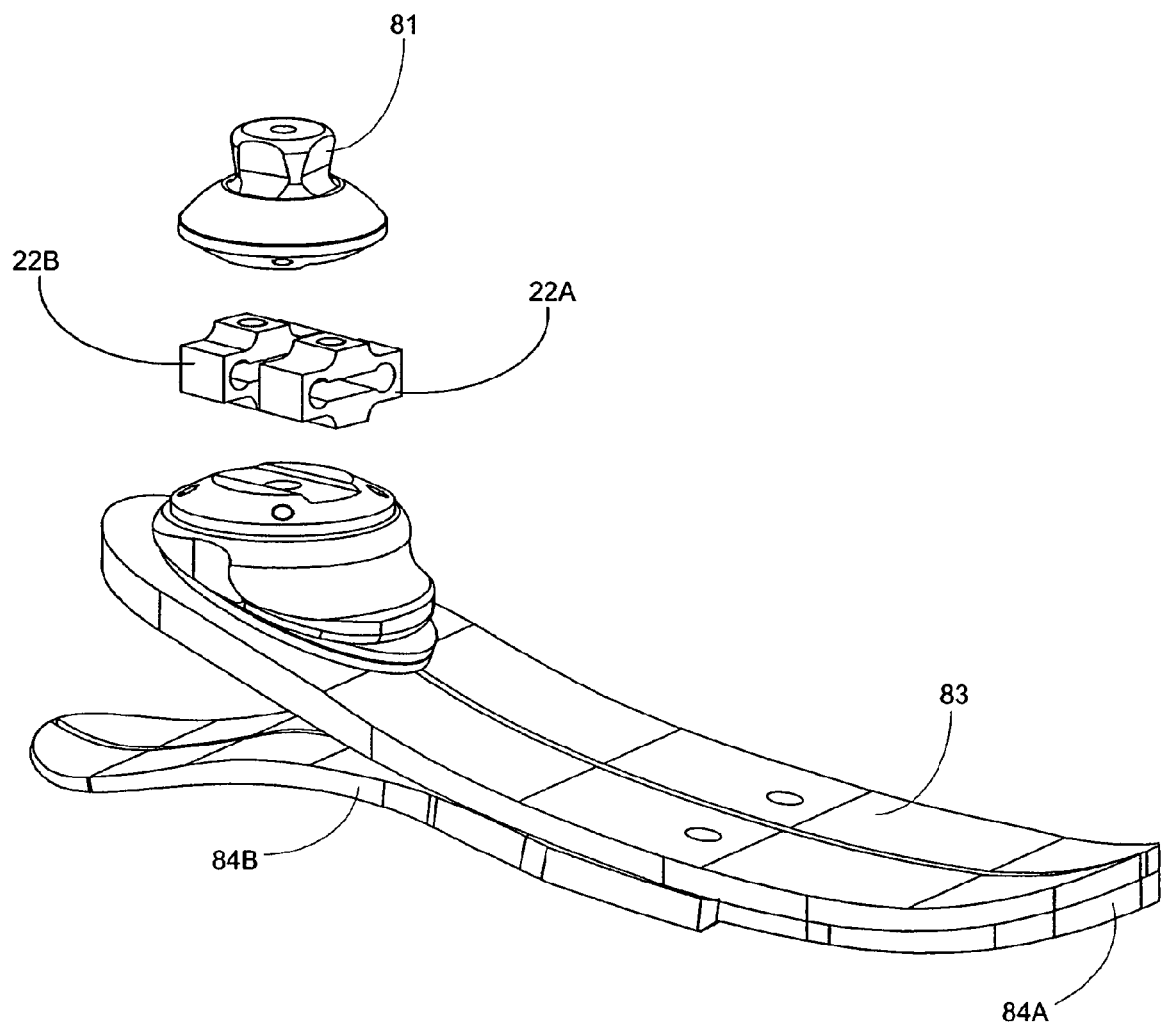
FIG. 11 is an exploded perspective view of the instrumented prosthetic foot of FIG. 10.

Following the previous discussion about the locations of sensors (22A, 22B), a further alternative embodiment of the instrumented prosthetic foot (20) is shown in FIGS. 10 and 11. The instrumented prosthetic foot (20) includes connector (81), foot plate (83), toe plate (84A) and heel plate (84B), such as provided by, for example, a Vari-Flex® prosthetic foot from Össur, and load cells (22A, 22B). Load cells (22A, 22B) are located below connector (91), load cell (22A) being slightly biased towards the toe area of the foot and load cell (22B) being slightly biased towards the heel area. Since the sensors (22A, 22B) are not located directly at the toe and heel areas, Equation 3 and Equation 4 may be used, for example by controller (40), to compute the equivalent pressures at the toe and heel areas by defining the equivalent torque at the ankle and the axial force at connector (81) as follows:

$$F\_conn\_meas = F\_22B + F\_22A \quad \text{Equation 5}$$

$$M\_ankle\_meas = F\_22B \cdot I\_22B - F\_22A \cdot I\_22A \quad \text{Equation 6}$$

Where
F_22B is the force measured at sensor 22B;
F_22A is the force measured at sensor 22A;
I_22B is the distance between the center of the connector (81) and the center of sensor 22B;
I_22A is the distance between the center of the connector (81) and the center of sensor 22A.

Figure 12:
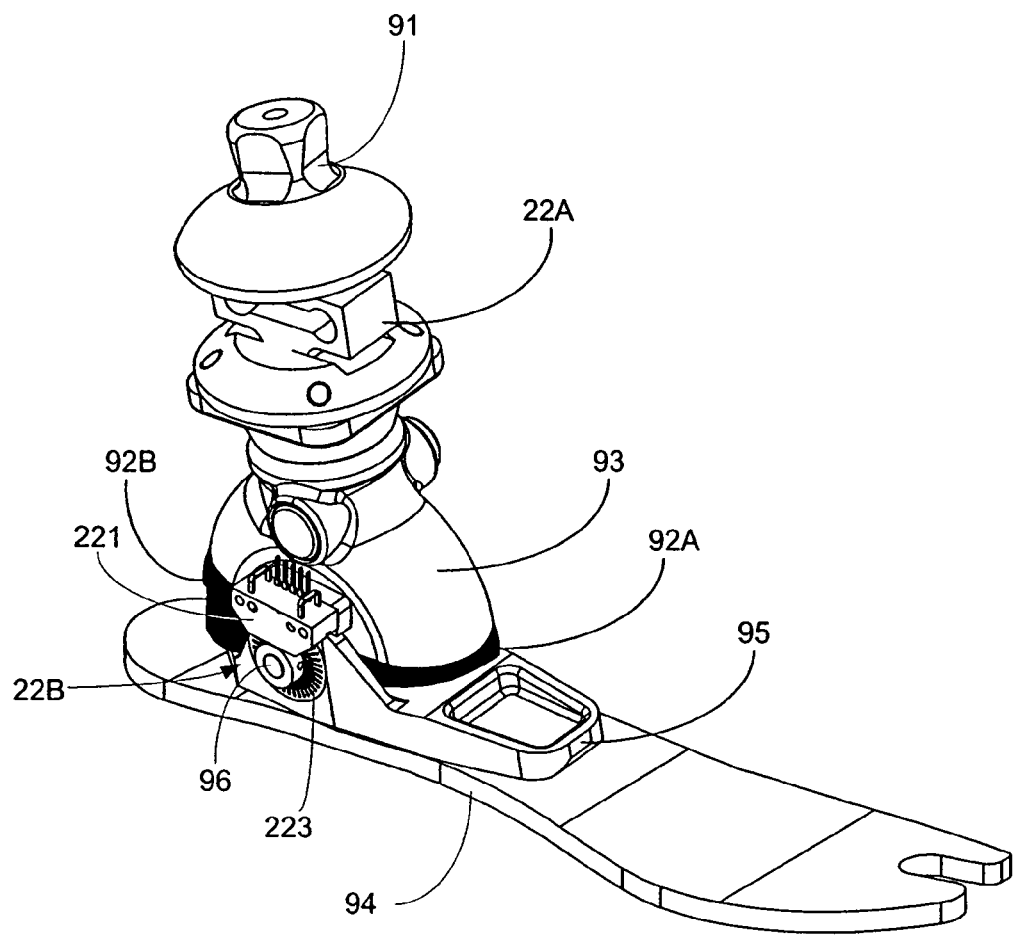
FIG. 12 is a perspective view, from the front and slightly above, of a yet further still alternative embodiment of the instrumented prosthetic foot of FIG. 3
Figure 13:
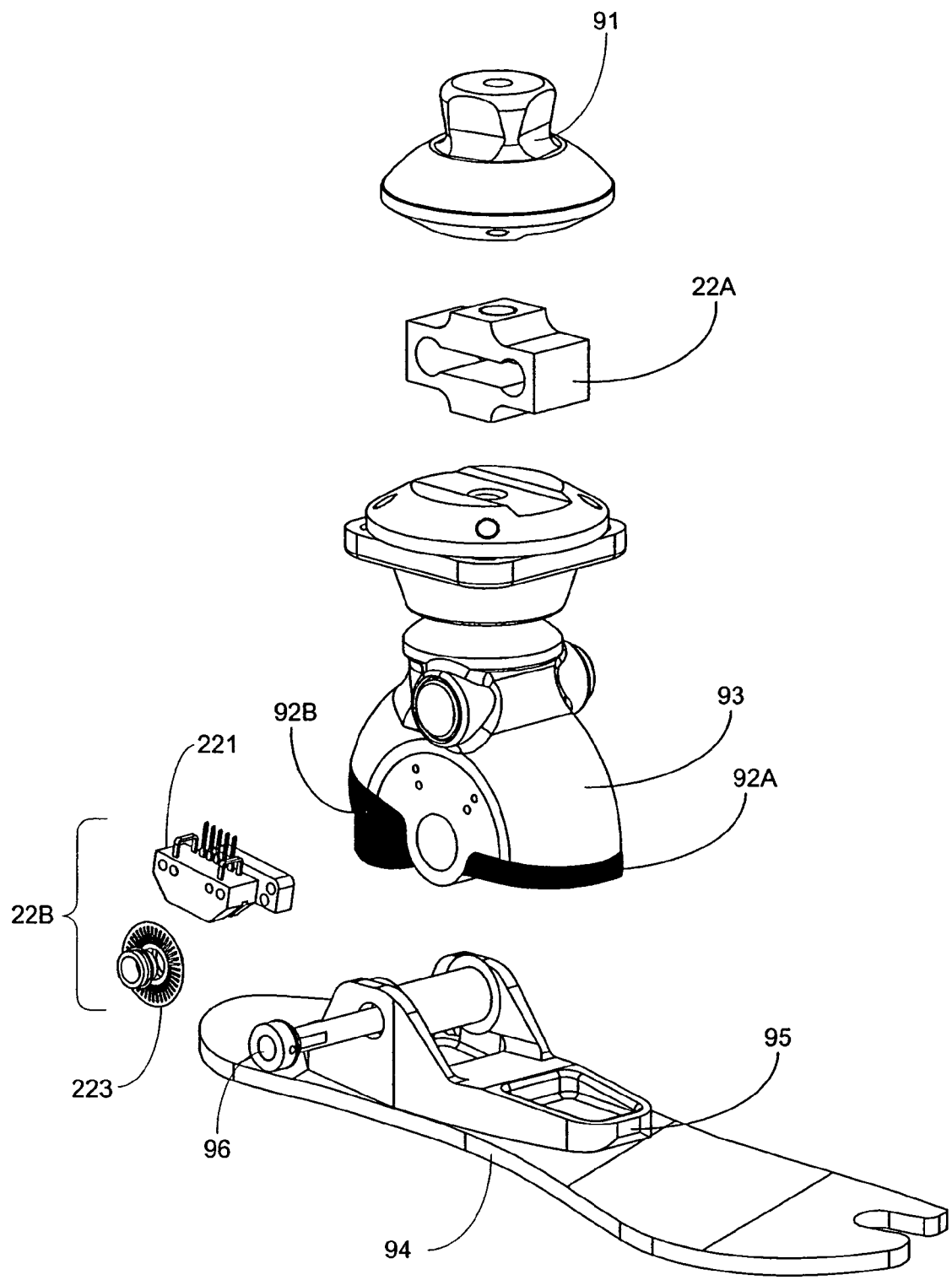
FIG. 13 is an exploded perspective view of the instrumented prosthetic foot of FIG. 12.

In the previous embodiments of the instrumented prosthetic foot (20), the force (or pressure) at the toe and heel areas, F_toe and F_heel respectively, was obtained either by positioning pressure sensors (22A, 22B) directly at those areas or by positioning pressure sensors or load cells (22A, 22B) in other areas and obtaining the equivalent information by computing the equivalent torque at the ankle and the axial force at the connector. Other types of sensors may also be used to obtain the equivalent torque at the ankle and the axial force at the connector. Such an example is illustrated by a further still embodiment of the instrumented prosthetic foot (20), which is shown in FIGS. 12 and 13. The instrumented prosthetic foot (20) includes connector (91), mounted on pivoting ankle (93). Bumpers (92A, 92B) are positioned between the pivoting ankle (93) and rocker plate (95) located on a foot plate (94). The pivoting ankle (93) is connected to the rocker plate (95) by a pivot pin (96). Such an arrangement is provided by, for example, an Elation® prosthetic foot from Össur. A load cell (22A) and an optical encoder (22B) are incorporated into the foot (20) to provide measurement of the distribution of forces along the foot (20). Load cell (22A) is positioned between connector (91) and pivoting ankle (93). Optical encoder (22B) comprises reader (221) and disk (223). Reader (221) is located on pivoting ankle (93) while disk (223) is located on rocker plate (95) and encircles pivot pin (96). Once again, Equation 3 and Equation 4 may be used, for example by controller (40), to compute the equivalent pressures at the toe and heel areas by defining the equivalent torque at the ankle and the axial force at connector (91) as follows:

$$F\_conn\_meas = F\_22A \quad \text{Equation 7}$$

$$M\_ankle\_meas = R\_ankle\_meas \cdot R\_const \quad \text{Equation 8}$$

Where

F_22A is the force measured at sensor 22A;

R_ankle_meas is the rotation measurement of pivoting ankle (93) about pivot pin (96) as measured by optical encoder (22B);

R_const is a constant associated with the resistance of bumpers (92A, 92B) to compression, which constant varies depending in the material used.

Figure 14:
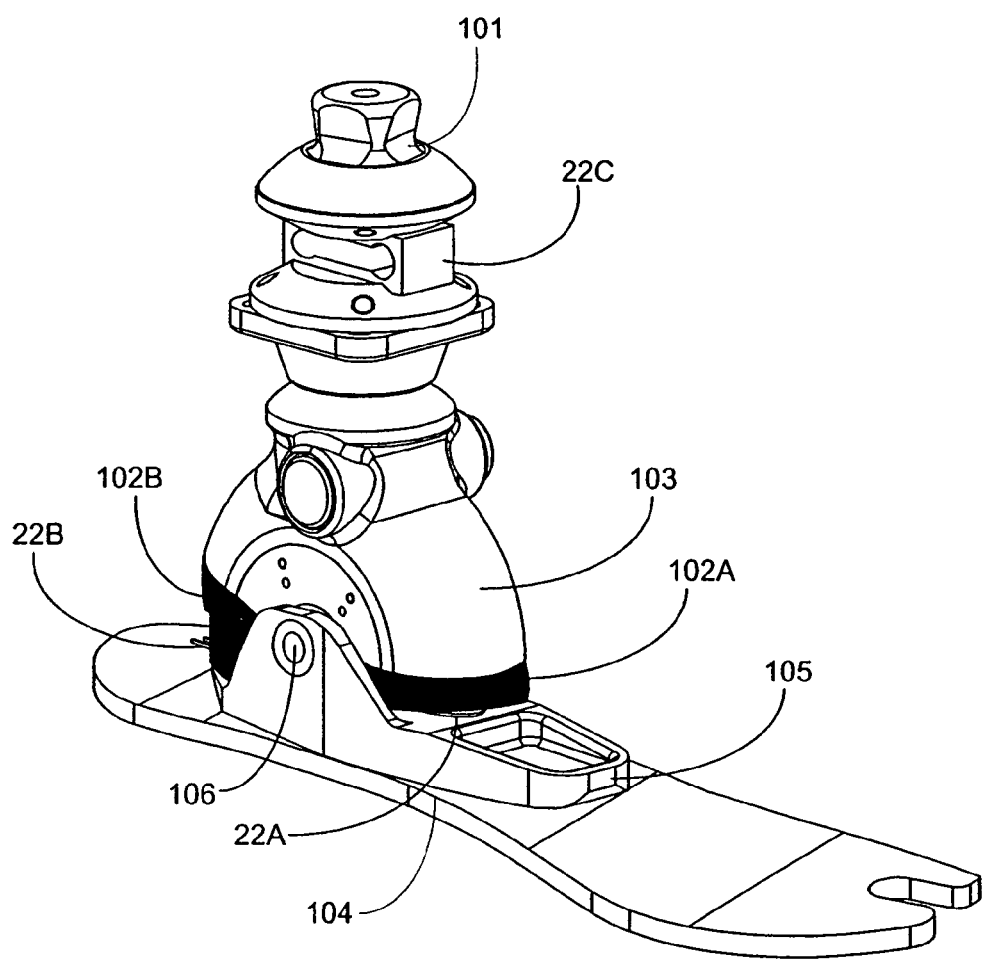
FIG. 14 is a perspective view, from the front and slightly above, of a further alternative embodiment of the instrumented prosthetic foot of FIG. 3
Figure 15:
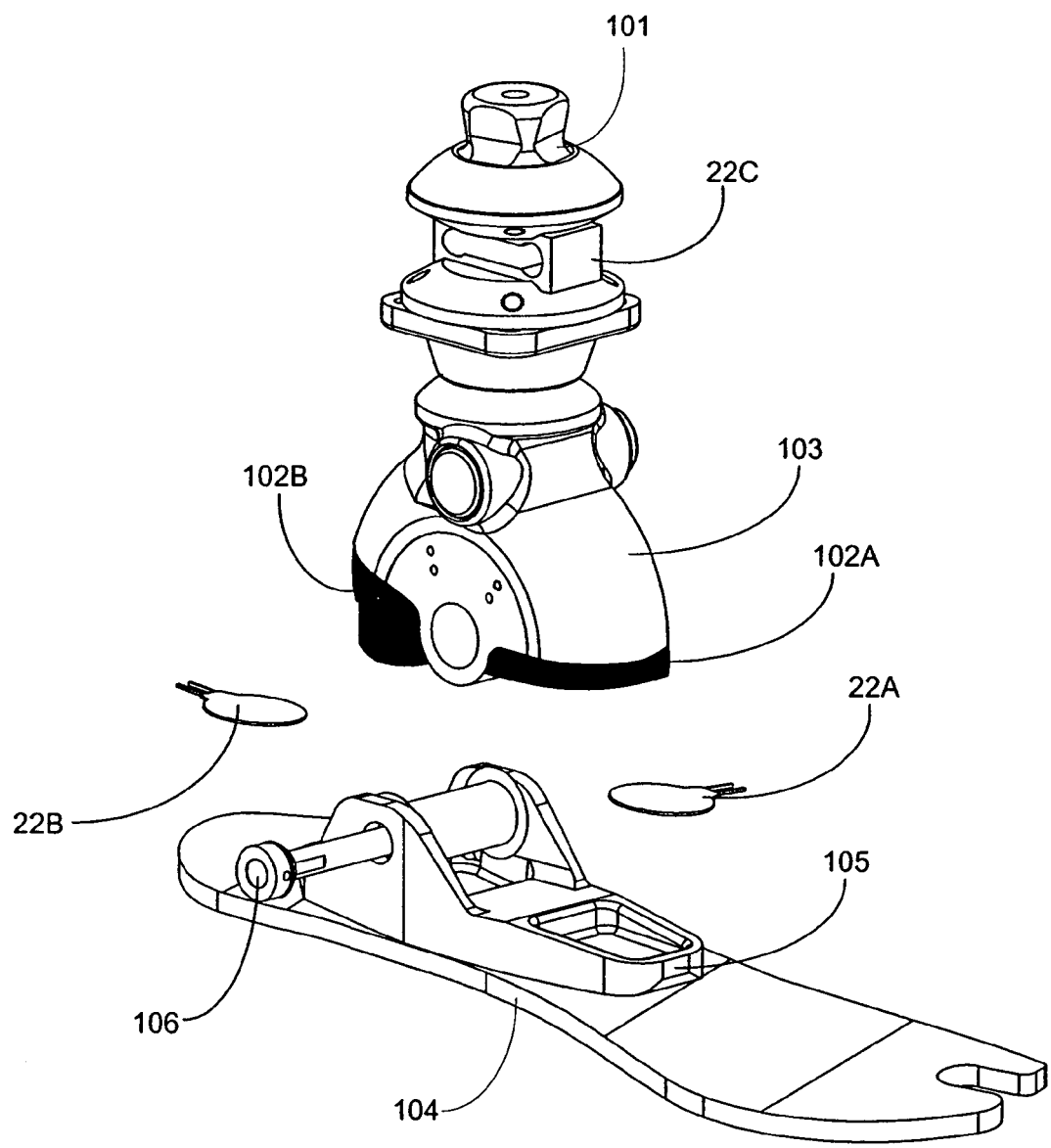
FIG. 15 is an exploded perspective view of the instrumented prosthetic foot of FIG. 14.

A yet further alternative embodiment of the instrumented prosthetic foot (20) is shown in FIGS. 14 and 15. The instrumented prosthetic foot (20) includes connector (101), mounted on pivoting ankle (103). Bumpers (102A, 102B) are positioned between the pivoting ankle (103) and rocker plate (105) located on a foot plate (104). The pivoting ankle (103) is connected to the rocker plate (105) by a pivot pin (106). Such an arrangement is provided by, for example, an Elation® prosthetic foot from Össur. Pressure sensors (22A, 22B) and load cell (22C) are incorporated into the foot (20) to provide measurement of the distribution of forces along the foot (20). Pressure sensor (22A) is positioned between rocker plate (85) and bumper (82A) while pressure sensor (22B) is positioned between rocker plate (85) and bumper (82B). A load cell (22C) is positioned between connector (91) and pivoting ankle (93).

In this embodiment, Equation 6 is used to compute the equivalent torque at the ankle, while the axial force at connector (101) is computed using the following equation:

$$F\_conn\_meas = F\_22C \quad \text{Equation 9}$$

Load cell (22C) is required to compute the axial force at connector (101) since when there is no torque at the ankle, i.e. the wearer of the prosthesis is standing still, the axial force is being exerted in its entirety onto pivot pin (96).

In all of the described embodiments, the sensors (22A, 22B) may be directly connected to interface (30) of control system (100) or indirectly using an intermediary system (not shown), for instance a wireless emitter. Of course, other types of communication link technologies may be used, such as, for example, optical.

Other types of non-articulated or articulated prosthetic foot may be used as well as long as the selected prosthetic foot provides approximately the same dynamical response as the ones mentioned here above. Nevertheless, an articulated foot offers the best performances. The instrumented prosthetic foot (20) may further have an exposed metal or composite structure or it may have a cosmetic covering that gives it the appearance of a human ankle and foot.

It should be noted that the present invention is not limited to its use with the mechanical configuration illustrated in FIG. 1 or the control system (100) illustrated in FIG. 2. It may be used with a leg prosthesis having more than one joint. For instance, it may be used with a prosthesis having an ankle joint, a metatarsophalangeal joint or a hip joint in addition to a knee joint. Moreover, instead of a conventional socket a osseo-integrated devices could also be used, ensuring a direct attachment between the mechanical component of the prosthesis and the amputee skeleton. Other kinds of prostheses may be used as well.

What is claimed is:

1. A prosthetic system for use with an above-knee amputee, the prosthetic system comprising:
   an actuatable knee member configured to be operably attached to an above-knee amputee at an upper portion and to a prosthetic foot and ankle system at a lower portion, the actuatable knee member being controlled by a controller;
   a prosthetic foot and ankle system comprising:
      a prosthetic foot comprising at least one elongated foot plate having a toe region and a heel region;
      an ankle structure pivotally connected to the prosthetic foot; and
      a connector configured to connect the prosthetic foot and ankle system to the actuatable knee member;
   a first sensor comprising an encoder configured to measure the rotation of the ankle structure about its pivot axis;
   a second sensor configured to measure an axial force at the connector of the prosthetic foot and ankle system; and
   an interface for transmitting signals from the first and second sensors to the controller, wherein the controller is configured to use the signals from the first and second sensors to control the actuatable knee member.

2. A prosthetic system according to claim 1, wherein the second sensor comprises a load cell.

3. A prosthetic system according to claim 1, further comprising a kinematic sensor configured to measure acceleration of the actuatable knee member.

4. A prosthetic system according to claim 1, wherein the prosthetic foot includes a pair of underfoot locations, the first location corresponding to the heel area of the human foot and second location corresponding to the toe area of the human foot.

5. A prosthetic system according to claim 4, further comprising first and second pressure sensors configured to provide measurement of a distribution of forces along the foot.

6. A prosthetic system according to claim 5, wherein the first and second pressure sensors are positioned between the prosthetic foot and the ankle structure.

7. A prosthetic system according to claim 1, wherein the second sensor is positioned between the ankle structure and the connector.

8. A prosthetic system according to claim 1, wherein the first sensor comprises an optical encoder positioned on the ankle structure about its pivot axis with the elongated body.

9. A prosthetic system according to claim 1, wherein the interface for transmitting signals from the first and second sensors to the controller is a wired connection.

10. A prosthetic system according to claim 1, wherein the interface for transmitting signals from the first and second sensors to the controller is a wireless connection.

11. A prosthetic system according to claim 1, wherein the actuatable knee member comprises a passive actuating mechanism.

12. A prosthetic system according to claim 1, wherein the actuatable knee member comprises an active actuating mechanism.

13. A prosthetic system for use with an above-knee amputee, the prosthetic system comprising:
   a knee joint prosthesis comprising an actuating mechanism;
   a controller for controlling the actuating mechanism; and
   a prosthetic foot and ankle system connected to the knee joint prosthesis and comprising:
      a prosthetic foot;
      an ankle structure pivotally connected to the prosthetic foot; and
      an ankle encoder positioned on the foot and ankle system and configured to measure rotation of the foot and ankle system about its pivot axis;
   a sensor for providing force measurements to the controller for controlling the actuating mechanism based on the force measurements; and
   wherein the actuating mechanism comprises an active actuating mechanism and the controller is configured to determine joint trajectories and a required angular force or torque of the knee joint prosthesis based on information from the ankle encoder and the sensor.

14. The prosthetic system of claim 13, wherein the sensor comprises a load cell, and the prosthetic system further comprises first and second pressure sensors configured to provide measurement of a distribution of forces along the prosthetic foot.

15. The prosthetic system of claim 13, wherein the sensor comprises a load cell for providing force measurements to the controller for controlling the actuating mechanism based on the force measurements.

16. The prosthetic system of claim 13, wherein the knee joint prosthesis comprises one or more kinematic sensors configured to measure an angle of the knee joint prosthesis.

17. The prosthetic system of claim 16, wherein the controller is configured to receive data from the one or more kinematic sensors of the knee joint prosthesis.

\* \* \* \* \*